(12) United States Patent
Suter et al.

(10) Patent No.: US 9,689,661 B2
(45) Date of Patent: Jun. 27, 2017

(54) APPARATUS AND METHOD TO COMPENSATE FOR INPUT POLARIZATION MODE VARIATION

(71) Applicant: The General Hospital Corporation, Boston, MA (US)

(72) Inventors: Melissa Suter, Charlestown, MA (US); David Adams, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/100,815

(22) PCT Filed: Dec. 3, 2014

(86) PCT No.: PCT/US2014/068382
§ 371 (c)(1),
(2) Date: Jun. 1, 2016

(87) PCT Pub. No.: WO2015/084964
PCT Pub. Date: Jun. 11, 2015

(65) Prior Publication Data
US 2016/0305762 A1   Oct. 20, 2016

Related U.S. Application Data

(60) Provisional application No. 61/911,164, filed on Dec. 3, 2013.

(51) Int. Cl.
*G01B 9/02* (2006.01)
*G02B 27/28* (2006.01)
(Continued)

(52) U.S. Cl.
CPC ...... *G01B 9/02011* (2013.01); *A61B 1/00165* (2013.01); *A61B 1/2676* (2013.01);
(Continued)

(58) Field of Classification Search
CPC ............ G01B 9/02011; G01B 9/02044; G01B 9/0209; G01B 9/02091; G01B 2290/70;
(Continued)

(56) References Cited

U.S. PATENT DOCUMENTS 5,254,112 A * 10/1993 Sinofsky ............ A61B 5/02007
600/439
8,705,167 B2    4/2014 Akasakya et al.
(Continued)

FOREIGN PATENT DOCUMENTS

JP    2008142443 A  *  6/2008

OTHER PUBLICATIONS

Suter, Melissa Jane et al. "Progress in Intracoronary Optical Coherence Tomography". IEEE Journal of Selected Topics in Quantum Electronics, vol. 16, No. 4, Jul./Aug. 2010, pp. 706-714.*
(Continued)

*Primary Examiner* — Michael A Lyons
(74) *Attorney, Agent, or Firm* — Andrews Kurth Kenyon LLP

(57) ABSTRACT

Exemplary apparatus and method can be provided. For example, with at least one first arrangement, it is possible to provide at least one first radiation, which can impact at least one second arrangement that is provided in an optical path between the at least one first arrangement(s) and at least sample. The second arrangement can have at least one birefringent property, In addition, with at least one detector third arrangement, it is possible to receive at least one second radiation from at least one first portion of the second arrangement(s), and at least one third radiation from at least one second portion of the second arrangement(s). The second and third radiations can be associated with the first radiation(s). Using at least one computing fourth arrange-
(Continued)

ment, it is possible to determine information regarding the first radiation(s) based on the second and third radiations.

25 Claims, 30 Drawing Sheets

(51) Int. Cl.
| | |
|---|---|
| G02B 6/27 | (2006.01) |
| A61B 5/00 | (2006.01) |
| A61B 1/00 | (2006.01) |
| A61B 1/267 | (2006.01) |
| G02B 6/36 | (2006.01) |

(52) U.S. Cl.
CPC .......... *A61B 5/0066* (2013.01); *G01B 9/0209* (2013.01); *G01B 9/02044* (2013.01); *G02B 6/278* (2013.01); *G02B 27/28* (2013.01); *G02B 6/3604* (2013.01)

(58) Field of Classification Search
CPC .............. G01B 9/0205; G01B 9/02055; G01B 9/02057; A61B 1/00165; A61B 1/2676; A61B 5/0066; A61B 5/0086
See application file for complete search history.

(56) References Cited

U.S. PATENT DOCUMENTS

| | | | | |
|---|---|---|---|---|
| 2002/0138073 | A1* | 9/2002 | Intintoli | A61B 18/22 606/15 |
| 2003/0058442 | A1 | 3/2003 | Garab et al. | |
| 2003/0184735 | A1 | 10/2003 | Kotten et al. | |
| 2007/0109554 | A1 | 5/2007 | Feldchtein et al. | |
| 2007/0236700 | A1 | 10/2007 | Yun et al. | |
| 2008/0267562 | A1* | 10/2008 | Wang | A61B 5/0062 385/31 |
| 2008/0291463 | A1* | 11/2008 | Milner | A61B 1/00096 356/491 |
| 2012/0050846 | A1* | 3/2012 | Akasaka | H04B 10/2507 359/344 |

OTHER PUBLICATIONS

International Written Opinion for International Application No. PCT/US2014/068382 mailed on Mar. 2, 2015.
International Search Report for International Application No. PCT/US2014/068382 mailed on Mar. 2, 2015.
Villiger M. et al., Spectral binning for mitigation of polarization mode dispersion artifacts in catheter-based optical frequency domain imaging. Opt Exp 2013, 21(14):16353-69.
Saxer CE. et al., High-speed fiber-based polarization-sensitive optical coherence tomography of in vivo human skin. Opt Lett 2000, 25(18):1355-1357.
Park B. et al., Real-time multi-functional optical coherence tomography. Opt Exp 2003, 11(7):782-793.
Yun SH. et al., Comprehensive volumetric optical microscopy in vivo. Nat Med 2006, 12(12):1429-1433.
Nadkarni SK. et al., Measurement of collagen . . . in atherosclerotic plaques using polarization-sensitive optical coherence tomography. J Am Coll Cardiol 2007, 49(13):1474-1481.
Woodruff, P.G., et al. Hyperplasia of smooth muscle in mild to moderate asthma without changes in cell size or gene expression. AJRCCM, 2004; 169: 1001-1006.
Castro, M., et al. Effectiveness & safety of bronchial thermoplasty . . . asthma: a multicenter, randomized, double-blind, sham-controlled clinical trial. AJRCCM, 2010; 181: 116-124.
Wenzel, S.E. Asthma phenotypes: the evolution from clinical to molecular approaches. Nature medicine, 2012; 18: 716-725.
Sittka, A., et al., Asthma phenotyping, therapy, and prevention: what can we learn from systems biology? Pediatric research, 2013; 73: 543-552.
Huang, D., et al. Optical coherence tomography. Science, 1991; 254: 1178-1181.
de Boer, J.F., et al. Two-dimensional birefringence imaging in biological tissue by polarization-sensitive optical coherence tomography. Optics letters 1997; 22: 934-936.
Hitzenberger, C., et al, Measurement and imaging of birefringence . . . orientation by phase resolved polarization sensitive optical coherence tomography. Opt Exp, 2001; 9: 780-790.
Oh, W.Y., et al. High-speed polarization sensitive optical frequency domain imaging with frequency multiplexing. Opt Exp., 2008; 16: 1096-1103.
Yun, S., et al. High-speed optical frequency-domain imaging. Opt Exp., 2003; 11: 2953-2963.
Zhang, E.Z. & Vakoc, B.J. Polarimetry noise in fiber-based optical coherence tomography instrumentation. Opt Exp., 2011; 19: 16830-16842.
Hsiung, P.L., et al., Effect of tissue preservation on imaging using ultrahigh resolution optical coherence tomography. Journal of Biomedical Optics, 2005; 10: 064033.
Bara, I., et al. Pathophysiology of bronchial smooth muscle remodelling in asthma. The European respiratory journal, 2010; 36: 1174-1184.
James, A. & Carroll, N. Airway smooth muscle in health and disease; methods of measurement and relation to function. European Respiratory Journal, 2000; 15: 782-789.
Smolensky, A.V., et al. Length-dependent filament formation assessed . . . increases during activation of porcine tracheal muscle. Jour of Physiology, 2005; 563: 517-527.
Yun, S., et al. Removing the depth-degeneracy in optical frequency domain imaging with frequency shifting. Optics Express, 2004; 12: 4822-4828.
Gordon, J.P. & Kogelnik, H. PMD fundamentals: polarization mode dispersion in optical fibers. Proceedings of the National Academy of Sciences of the USA, 2000; 97: 4541-4550.

\* cited by examiner

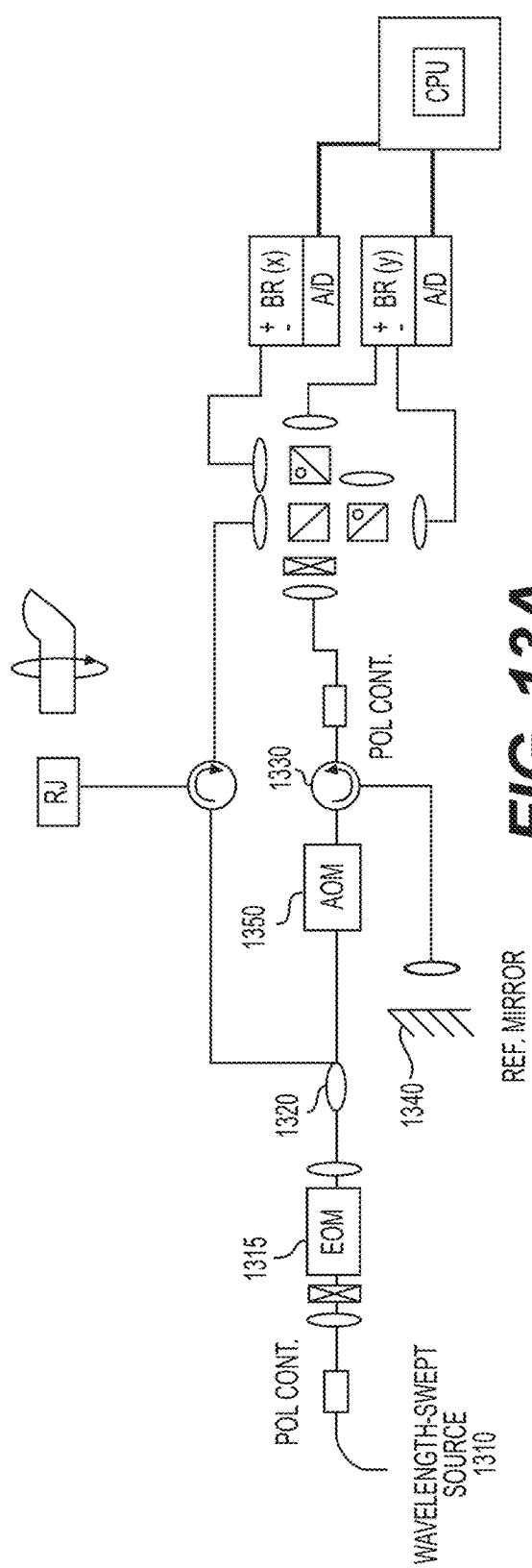
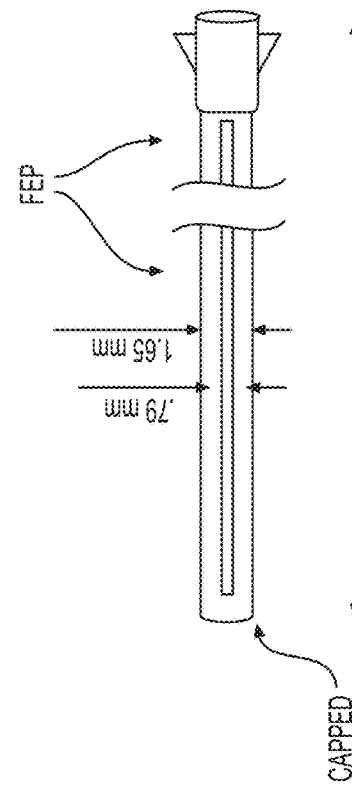
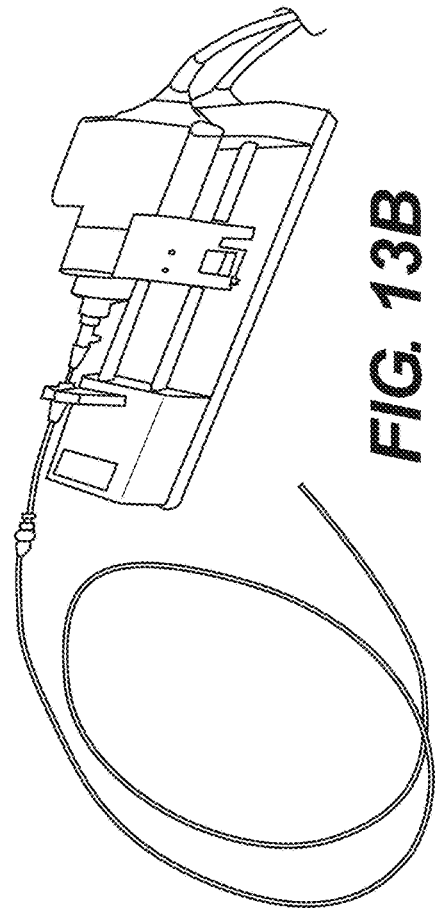
FIG. 13A
FIG. 13B
FIG. 13C

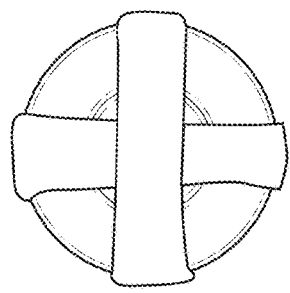
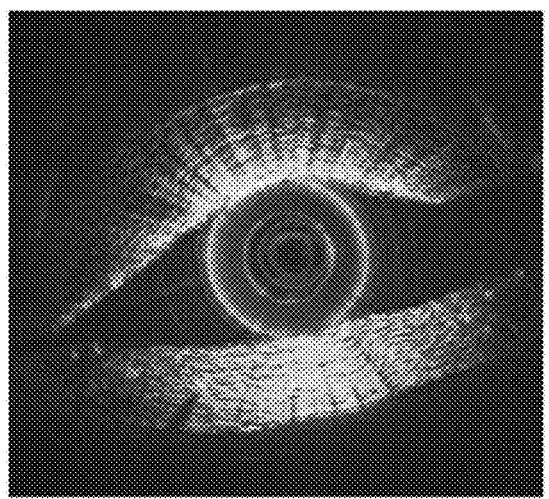
FIG. 17A
FIG. 17B
FIG. 17C

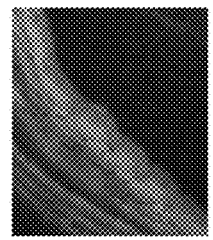
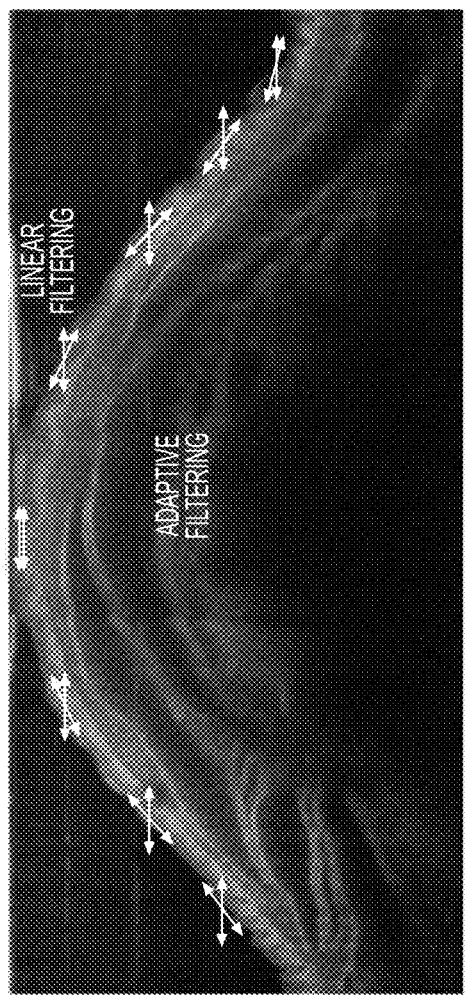
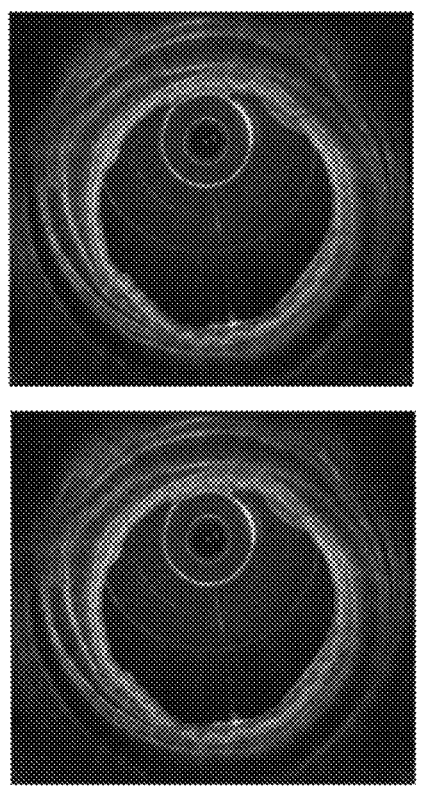
FIG. 19D
FIG. 19E
FIG. 19A
FIG. 19C
FIG. 19B

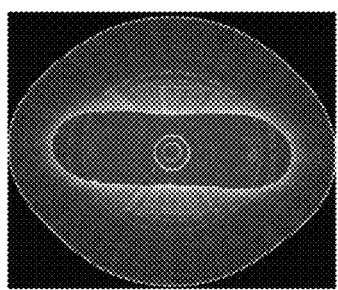
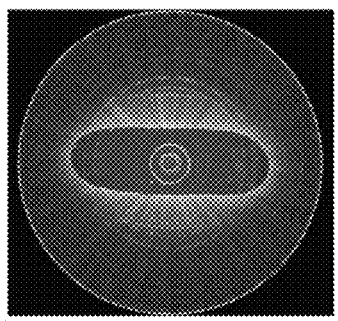
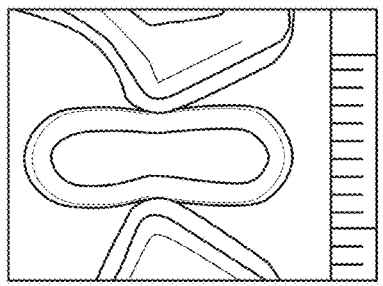
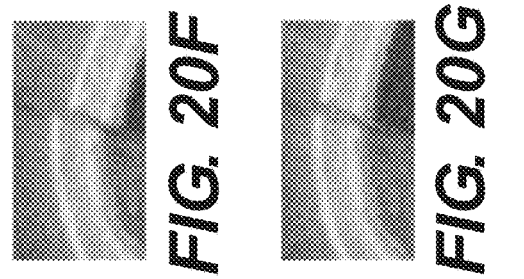
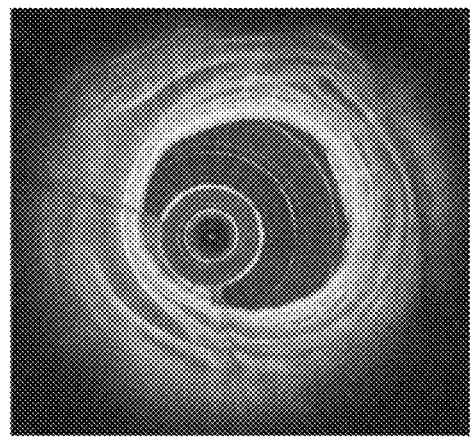
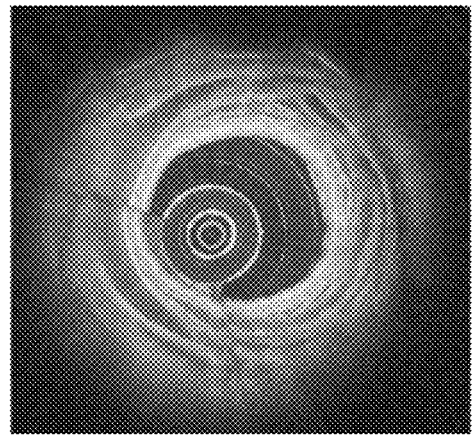

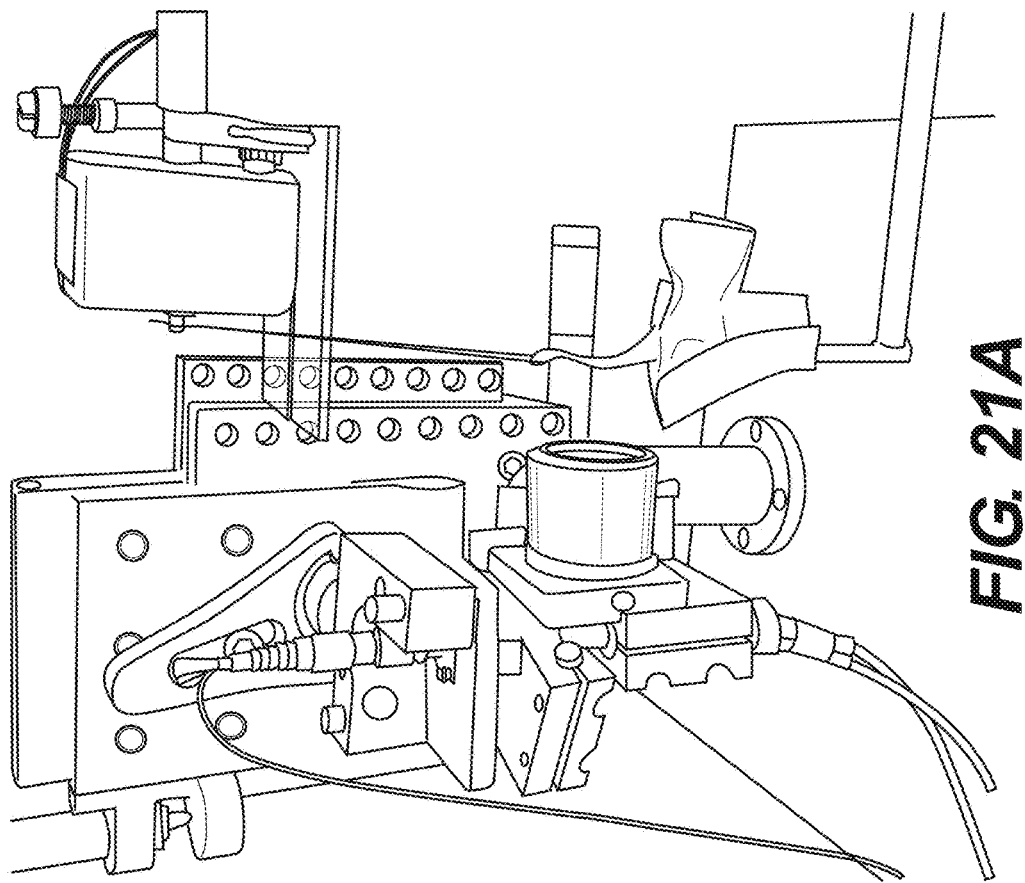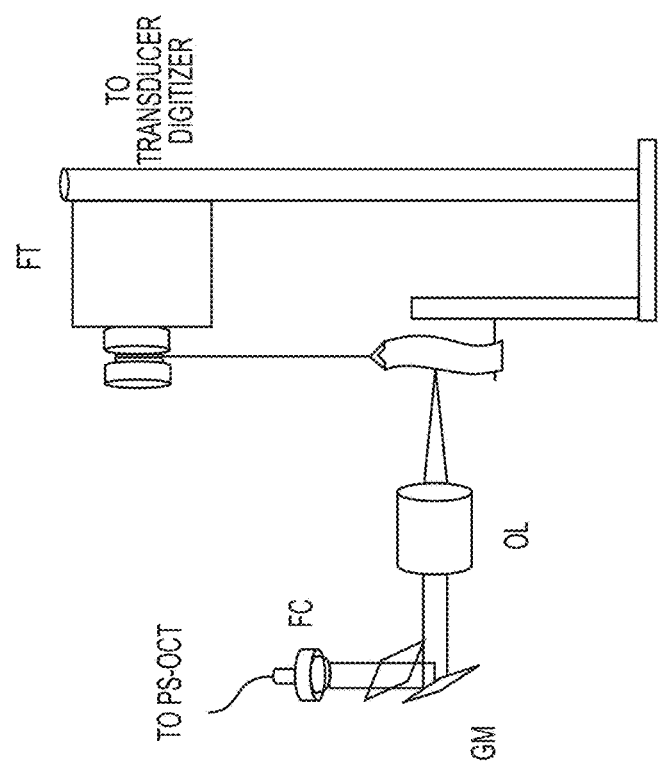
FIG. 21A
FIG. 21B

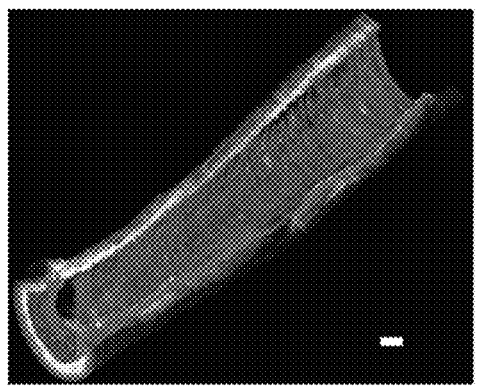 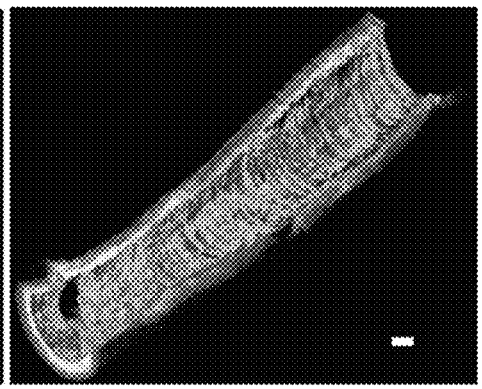
FIG. 22A  FIG. 22B
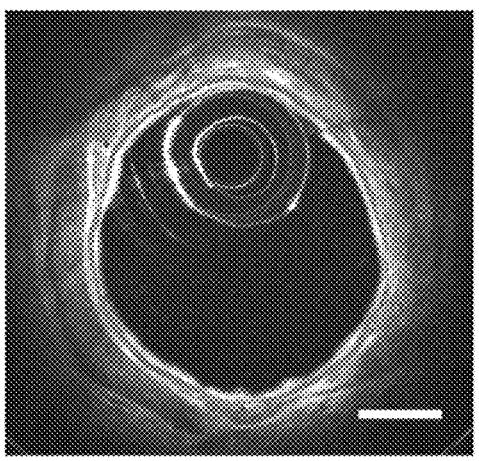 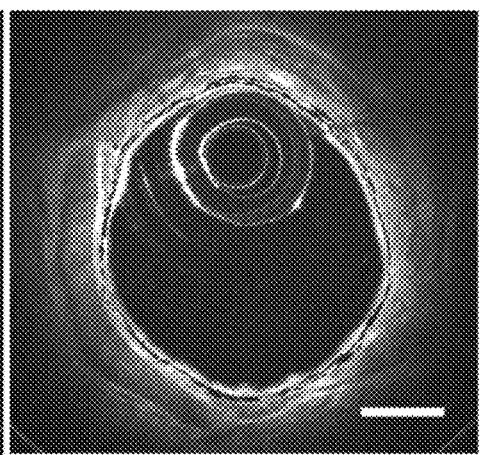
0  1 0  28
g/100μm
FIG. 22C  FIG. 22D

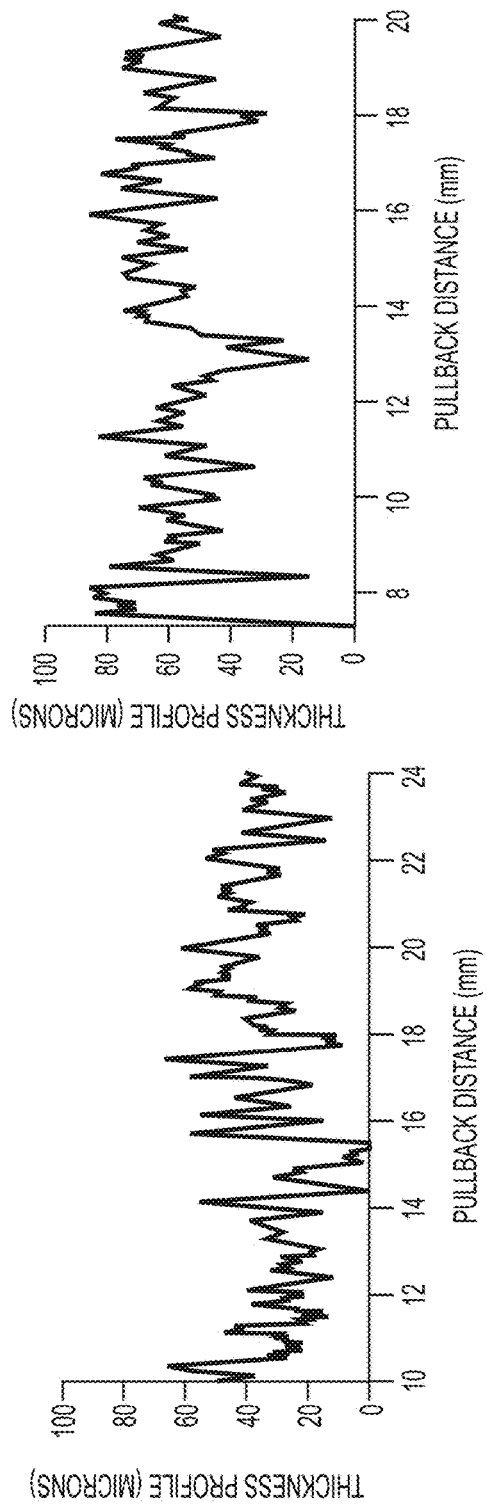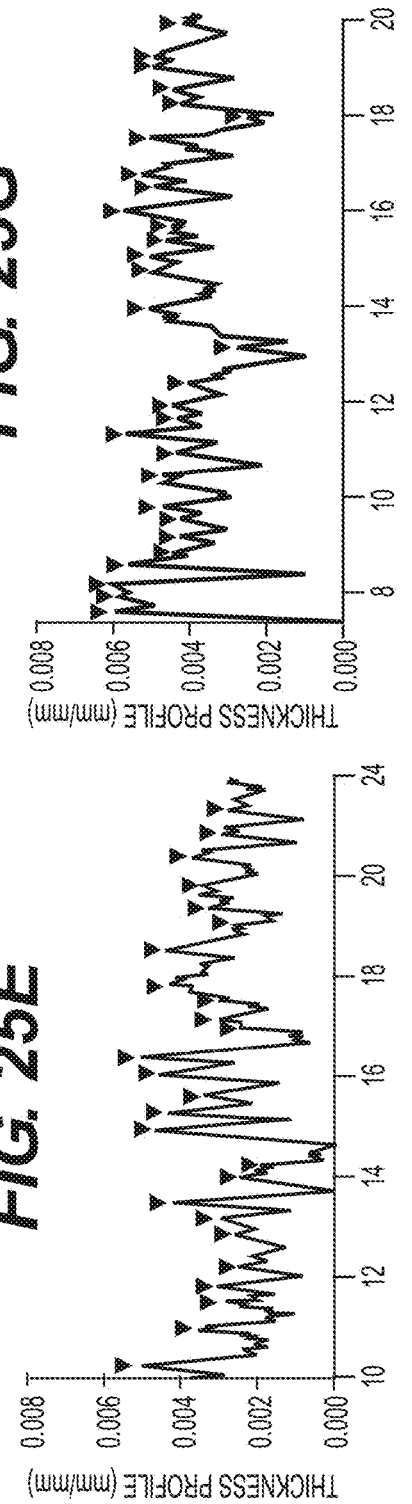

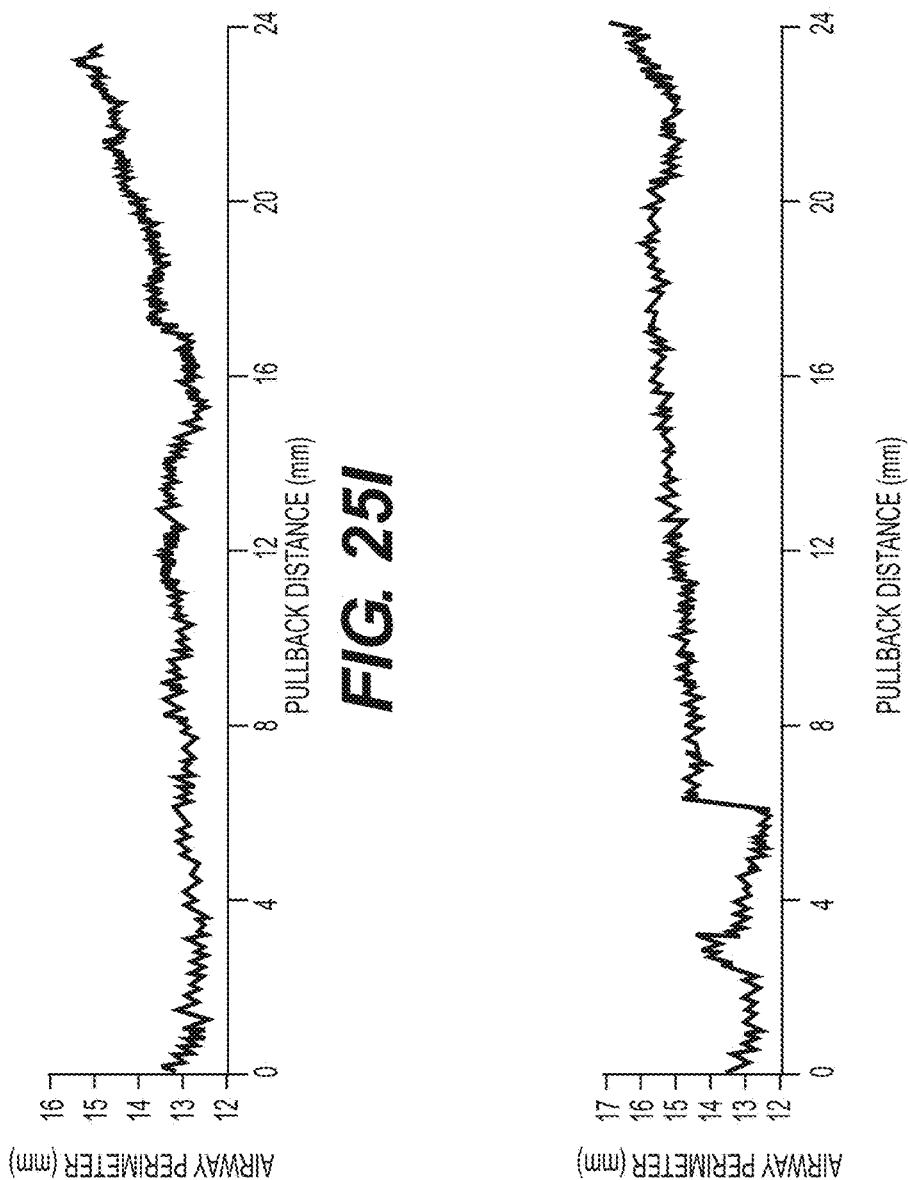

APPARATUS AND METHOD TO COMPENSATE FOR INPUT POLARIZATION MODE VARIATION

CROSS-REFERENCE TO RELATED APPLICATION(S)

The present application relates to and claims priority from International Patent Application No. PCT/2014/068382, filed on Dec. 3, 2014, and from U.S. Patent Application Ser. No. 61/911,164, filed on Dec. 3, 2013, the entire disclosures of which are incorporated herein by reference.

FIELD OF THE DISCLOSURE

The present disclosure relates to apparatus and method for polarization compensation, and more particularly to exemplary embodiments of apparatus, systems and methods for compensating for variation in the input polarization mode that occurs in a polarization-sensitive optical frequency domain imaging (PS-OFDI) system.

BACKGROUND INFORMATION

Optical coherence tomography ("OCT") is an imaging technique that can measure an interference between a reference beam of light and a beam reflected back from a sample. A detailed system description of traditional time-domain OCT is described in Huang et al., "Optical Coherence Tomography," Science 254, 1178 (1991). Optical frequency domain imaging ("OFDI") techniques, which can be also known as swept source or Fourier-domain optical coherence tomography (OCT) techniques, can be OCT procedures which generally use swept laser sources. For example, an optical beam is focused into a tissue, and the echo time delay and amplitude of light reflected from tissue microstructure at different depths are determined by detecting spectrally resolved interference between the tissue sample and a reference as the source laser wavelength is rapidly and repeatedly swept. A Fourier transform of the signal generally forms an image data along the axial line (e.g., an A-line). A-lines are continuously acquired as the imaging beam is laterally scanned across the tissue in one or two directions that are orthogonal to the axial line.

The resulting two or three-dimensional data sets can be rendered and viewed in arbitrary orientations for gross screening, and individual high-resolution cross-sections can be displayed at specific locations of interest. This exemplary procedure allows clinicians to view microscopic internal structures of tissue in a living patient, facilitating or enabling a wide range of clinical applications from disease research and diagnosis to intraoperative tissue characterization and image-guided therapy. Exemplary detailed system descriptions for spectral-domain OCT and Optical Frequency Domain Interferometry are described in International Patent Application PCT/US03/02349 and U.S. Patent Application Ser. No. 60/514,769, respectively.

A contrast mechanism in the OFDI techniques can generally be an optical back reflection originating from spatial reflective-index variation in a sample or tissue. The result can be a so-called an "intensity image" that may indicate the anatomical structure of tissue up to a few millimeters in depth with spatial resolution ranging typically from about 2 to 20 μm. While the intensity image can provide a significant amount of morphological information, birefringence in tissues may offer another contrast useful in several applications such as quantifying the collagen content in tissue and evaluating disease involving the birefringence change in tissue. Polarization-sensitive OCT can provide an additional contrast by observing changes in the polarization state of reflected light. The first fiber-based implementation of polarization-sensitive time-domain OCT is described in Saxer et al., "High-speed fiber-based polarization-sensitive optical coherence tomography of in vivo human skin," Opt. Lett. 25, 1355 (2000).

In polarization-sensitive time-domain OCT techniques, a simultaneous detection of interference fringes in two orthogonal polarization channels can facilitate a complete characterization of a reflected polarization state, as described in J. F. de Boer et al., "Determination of the depth-resolved Stokes parameters of light backscattered from turbid media by use of polarization-sensitive optical coherence tomography," Opt. Lett. 24, 300 (1999). There can be two non-depolarizing polarization parameters: birefringence, characterized by a degree of phase retardation and an optic axis orientation, and diattenuation, which can be related to dichroism and characterized by an amount and an optic axis orientation. Together, these optical properties may be described by, e.g., the 7 independent parameters in the complex 2×2 Jones matrix.

The polarization state reflected from the sample can be compared to the state incident on the sample quite easily in a bulk optic system, as the polarization state incident on the sample can be controlled and fixed. However, an optical fiber may have a significant disadvantage in that a propagation through optical fiber can alter the polarization state of light. In this case, the polarization state of light incident on the sample may not be easily controlled or determined. In addition, the polarization state reflected from the sample may not be necessarily the same as the polarization state received at the detectors. Assuming negligible diattenuation, or polarization-dependent loss, optical fiber changes the polarization states of light passing through such fiber in such a manner as to preserve the relative orientation between states. The overall effect of propagation through optical fiber and non-diattenuating fiber components can be similar to an overall coordinate transformation or some arbitrary rotation. In other words, the relative orientation of polarization states at all points throughout propagation can be preserved, as described in U.S. Pat. No. 6,208,415.

There have been a number of approaches that can take advantage to determine the polarization properties of a biological sample imaged with polarization-sensitive OCT. Such approaches have suffered from some disadvantage, however.

For example, a vector-based method has been used to characterize birefringence and optic axis orientation only by analyzing rotations of polarization states reflected from the surface and from some depth for two incident polarization states perpendicular in a Poincaré sphere representation as described in the Saxer Publication, J. F. de Boer et al., "Determination of the depth-resolved Stokes parameters of light backscattered from turbid media by use of polarization-sensitive optical coherence tomography," Opt. Lett. 24, 300 (1999), and B. H. Park et al., "In vivo burn depth determination by high-speed fiber-based polarization sensitive optical coherence tomography," J. Biomed. Opt. 6, 474 (2001).

Mueller matrix based methods are capable of determining birefringence, diattenuation, and optic axis orientation as described in S. L. Jiao et al., "Two-dimensional depth-resolved Mueller matrix of biological tissue measured with double-beam polarization-sensitive optical coherence tomography," Opt. Lett. 27, 101 (2002), S. Jiao et al., "Optical-fiber-based Mueller optical coherence tomography," Opt. Lett. 28, 1206 (2003), and S. L. Jiao et al., "Depth-resolved two-dimensional Stokes vectors of backscattered light and Mueller matrices of biological tissue measured with optical coherence tomography," Appl. Opt. 39, 6318 (2000). These typically utilize a multitude of measurements using a combination of incident states and detector settings and limits their practical use for in vivo imaging.

Jones matrix based approaches have also been used to characterize the non-depolarizing polarization properties of a sample as described in S. Jiao et al., "Optical-fiber-based Mueller optical coherence tomography," Opt. Lett. 28, 1206 (2003) and S. L. Jiao and L. V. Wang, "Jones-matrix imaging of biological tissues with quadruple-channel optical coherence tomography," J. Biomed. Opt. 7, 350 (2002). The description of these approaches has limited a use of optical fiber and fiber components such as circulators and fiber splitters such that these components must be traversed in a round-trip fashion and assumes that sample birefringence and diattenuation share a common optic axis. These approaches can use a multitude of measurements using a combination of incident states and detector settings and limits their practical use for in vivo imaging.

Generally, in nearly all of polarization sensitive time domain, Spectral Domain OCT, or OFDI systems, the polarization properties can be measured using different incident polarization states on the sample in a serial manner, i.e. the incident polarization state incident on the sample was modulated as a function of time.

Exemplary system and method for obtaining polarization sensitive information is described in U.S. Pat. No. 6,208, 415. Exemplary OFDI techniques and systems are described in International Application PCT/US04/029148. Method and system to determine polarization properties of tissue is described in International Application PCT/US05/039374.

For example, rotation and/or translation of an imaging catheter can give rise to rotations of a polarization mode along single mode optic fibers used to guide electromagnetic radiation (e.g., light). This can occurs within a single rotation of the imaging catheter, and can therefor therefore impact the uniformity of the input polarization state within a single imaging frame, making it impossible to reconstruct accurate information about the orientation of birefringent tissue that would otherwise be available.

Polarization sensitive optical coherence ("PS-OCT") technology imaging in fiber-based systems typically calculate the magnitude of birefringence while disregarding the vectorial aspect of the acquired data. This is because in single mode fibers random variations in the shape of the fiber core, either innate or due to external stress/strain, result in additional birefringence that renders absolute measurements of sample birefringence impossible. Instead, differential measurements of sample birefringence can be required starting at the sample surface, which serves as a calibration reflector. As a result, the magnitude of the birefringence can be recovered, although the orientation may be lost. Attempts to recover this information have heretofore involved using polarization—maintaining fibers [see, e.g., Ref 1] or placing bulk waveplates in the field of view between the imaging lens and sample to calibrate the orientation of the probing light [see, e.g., Ref. 2]. While these approaches can be successful when imaging via a bench top microscope configuration, neither is applicable when performing catheter imaging in in vivo applications. In addition, catheter imaging can be further complicated because the rotation of the catheter affects the measured orientation over the course of a single frame, so that from A-line to A-line the measured state is spuriously altered.

In systems that operate as described above, polarizing beam splitters send orthogonal components of the interference signal to two detectors, allowing the Jones vector to be determined. The signal is related to the source field by $$E_f = \begin{pmatrix} E_{fx}e^{i\varphi_{fx}} \\ E_{fy}e^{i\varphi_{fy}} \end{pmatrix} = e^{i\theta} J_{out} J_S J_{in} \begin{pmatrix} E_{\theta x}e^{i\varphi_{\theta x}} \\ E_{\theta y}e^{i\varphi_{\theta y}} \end{pmatrix}$$

where the J's$_S$ represent the Jones matrices of the output path, the sample, and the input path, respectively, and θ is the common phase. At a reference reflecting surface is $J_S=1$. Birefringence measurements at greater depths in the sample arm can then be related to this calibration measurement to yield the Jones matrix $J_A=J_{out}J_S J^{-1}_{out}$. Assuming no diattenuation exists in the system, $J_{out}$ represents a unitary transformation and therefore the relative retardance and optic axis of the sample may be extracted straightforwardly. The absolute orientation in the laboratory frame is, however, completely obliterated by the effect $J_{out}$ has on the measurements.

In the processing of the raw data, the complex components of the Jones vector measured by such system can be converted into the Stokes parameters Q, U, and V, with Q and U representing the basis vectors of linearly polarized states and V that of circularly polarized states. Since all sample data are acquired in the reflection configuration and therefore involve round—trip measurements, circular birefringence cannot be detected due to the round—□trip cancellation of any circularly birefringent signal. The physical orientations corresponding to the remaining Stokes parameters Q and U are depicted in FIG. 6.

The technique used to extract the principal axis has been described in a number of publications [see, e.g., Refs. 3-5]. For example, it is possible to alternate between two input polarization states that are orthogonal on the Poincare sphere. Switching between the two input states occurs at a frequency that is half that at which the system acquires A-lines, so that each successive pair of A-lines together form a single birefringence measurement at a (roughly) identical location in the sample. The relative axis can then be determined by calculating the pair of difference Stokes vectors along the axial profile to find how the polarization states were rotated and taking the cross product in order to identify the direction vector that gave rise to the rotations. This can correspond to the optic axis of the tissue at that depth in the sample.

Although it is well-established that airway smooth muscle (ASM) abnormality is a primary pathophysiologic mechanism in asthma, clinical asthma research has predominately neglected the contribution of ASM in favor of focusing on other factors such as airway inflammation. This can be largely due to the lack of means for adequately assessing ASM in vivo. Asthma is a widespread problem affecting hundreds of millions of people, approximately 10% of which are estimated to suffer from uncontrolled or poorly controlled symptoms. The difficulty in providing an asthma patient with the proper treatment can be in part due to a lack of understanding with regards to the pathophysiology of asthma, and the challenges currently faced in gaining such knowledge. While it is believed that ASM proliferation is intimately connected to the airway hyper-responsiveness experienced by sufferers of asthma [see, e.g., Refs. 8-10], the full extent of the connection between asthma and ASM abnormality has proved difficult to assess, largely because there has existed no imaging technology with the spatial and temporal resolution necessary to visualize ASM distribution and dynamics in vivo. The situation is further complicated by the fact that, as we now know, asthma itself is not a single disease but rather a collection of phenotypes [see, e.g., Refs. 11 and 12].

Among currently available imaging modalities, optical coherence tomography (OCT) [see, e.g., Ref. 13] offers what is arguably the most promising balance of technological features for undertaking fully non-invasive, in vivo studying of ASM and asthma. However, structural OCT still lacks the contrast necessary to discriminate ASM bands on a level approaching that of histological staining. One potential approach to overcoming this is to take advantage of the form birefringence of ASM fibers by utilizing polarization sensitive imaging. Form birefringence is the quantifiable anisotropy of ordered material structure manifested in the differential propagation time of orthogonal polarization states of light transmitted through the structure. Polarization sensitive OCT (PS-OCT) introduces a way of obtaining information about this anisotropy, bringing additional contrast to standard OCT images [see, e.g., Refs. 14-17].

Accordingly, there may be a need to address and/or overcome at least some of the issues of deficiencies described herein above.

SUMMARY OF EXEMPLARY EMBODIMENTS

It is one of the objects of the present disclosure to reduce or address the deficiencies and/or limitations of such prior art approaches, procedures, methods, systems, apparatus and computer-accessible medium.

To that end, exemplary apparatus, systems and methods according to exemplary embodiments of the present disclosure can be provided for compensating for a variation in the input polarization mode that can occurs in a polarization-sensitive optical frequency domain imaging (PS-OFDI) system, e.g., during an in vivo catheter based imaging procedure.

According to an exemplary embodiment of the present disclosure, using the exemplary apparatus, systems and/or methods, it is possible to compensate for a non-uniformity described herein above by, e.g., measuring a polarization state of the radiation (e.g., the light) reflected from inner and outer surfaces of a sheath which are used to protect the imaging catheter. The sheath, which can be comprised of extruded plastic, can exhibit some degree of birefringence which can effects the rotation of the polarization state of the radiation and/or the light along a fixed axis. The sheath can be substantially or nearly transparent, although reflections from its surface(s) can be used to calculate or otherwise determine the axis of the rotation thereof or of the catheter. Such exemplary configuration can provide a fixed reference point along the imaged frame to which all input states can be rotated, thus facilitating an unambiguous correction of the component of the input polarization along the optic axis of the sheath.

For example, exemplary embodiments of the apparatus, systems and/or methods according to the present disclosure facilitate a compensation for input polarization mode variation with the PS-OFDI system that can utilize catheter imaging procedure(s). Since bench top imaging can likely be used only for ex vivo tissue imaging, the exemplary apparatus, systems and/or methods can facilitates a polarization mode correction for the use with in vivo tissue imaging.

One of the exemplary advantages of the apparatus, systems and/or methods according to the exemplary embodiment of the present disclosure can be that they use only of what is already present in the imaging system, without additional materials and/or optics to achieve the compensation. This can indicate that there is likely little or no sacrifice in image quality and/or catheter dimensions. Further, the computational requirements of the correction procedure can be minimal, and therefore it is possible that such exemplary apparatus, systems and/or methods can be implemented in real time.

For example, the calculated Stokes parameters for tissue of uniform orientation generally change over the course of a single catheter rotation. This is a direct consequence of the constantly shifting nature of $J_{out}$ in catheter-based imaging and has nothing to do with the sample itself. According to certain exemplary embodiments of the present disclosure, it is possible to at least partially correct for this spurious alteration as well as extract some information about the actual orientation of the birefringent tissue. Such exemplary system and method can accurately resolve the Q component of the Stokes vector in the sample frame. For example, the functionality can be based on utilizing polarization signals from the catheter sheath. The sheath, being, e.g., a constant, fixed presence in exemplary catheter-based measurements, can serve as a preferable reference for extracting orientation data. The sheath can be comprised of extruded polymer—a nearly transparent material that nevertheless exhibits trace amounts of birefringence along its circumferential axis, this axis corresponding to the +Q Stokes parameter for both the sheath and the tissue being imaged. By comparing sequential signals from the sheath along the rotation of the catheter, e.g., it is then possible to compensate for the shifting of the measured birefringence orientation for the sheath and, as a result of the similarity between the plurality of sets of signals, the sample tissue itself.

According to certain exemplary embodiments of the present disclosure, method and system can be provided for obtaining partial information about the orientation of birefringent tissue in catheter—□based optical frequency domain imaging (OFDI). Such exemplary system and method can utilize a birefringence of the catheter sheath about its circumferential axis to accurately obtain the components of the orientation of birefringent tissue along the axes parallel (circumferential) and perpendicular (longitudinal) to the catheter sheath's optic axis. The exemplary method and system can be advantageous in that they do not require the use of additional experimental components, and can obtain optic axis information in catheter—□ based imaging.

According to an exemplary embodiment of the present disclosure, it is possible to utilize and/or extend the functionality of polarization sensitive OCT (PS-OCT) to provide an exemplary platform which can leverage the form birefringence of ASM fibers in such a way as to render ASM band structure and function mostly or wholly quantifiable, e.g., in vivo and over significant lengths of the airway.

Indeed, it is possible to utilize such exemplary embodiments of the present disclosure to, e.g., assess ASM distributions, visualize and characterize volumetric representations of ASM in in vivo airways, and correlate force of contraction with an increase in fiber retardation. Based on such exemplary results, it is possible to obtain and compile ASM band structure data from asthmatic and non-asthmatic human volunteers, and quantify band parameters that have previously been undetectable.

According to another exemplary embodiment of the present disclosure, exemplary system and method can be provided to measure the degree of anisotropy and the orientation of the fibers, thus facilitating and/or accounting for a significant enhanced birefringent fiber isolation and sensitivity. With this exemplary imaging platform, it is possible to accurately assess and measure the contractility of ASM by correlation with, e.g., histology and force measurements. It is further possible to utilize such exemplary technology to perform ASM band parameter analysis, e.g., in asthmatic and non-asthmatic airways with data obtained in vivo from healthy human volunteers.

Thus, exemplary apparatus and method can be provided according to an exemplary embodiment of the present disclosure. For example, with at least one first arrangement, it is possible to provide at least one first radiation, which can impact at least one second arrangement that is provided in an optical path between the at least one first arrangement(s) and at least sample. The second arrangement can have at least one birefringent property, In addition, with at least one detector third arrangement, it is possible to receive at least one second radiation from at least one first portion of the second arrangement(s), and at least one third radiation from at least one second portion of the second arrangement(s). The second and third radiations can be associated with the first radiation(s). Using at least one computing fourth arrangement, it is possible to determine information regarding the first radiation(s) based on the second and third radiations.

For example, the information can include an optical axis of the second arrangement. The third arrangement can further receive at least one fourth radiation from the sample(s), and generate data regarding the sample(s) using the information and the radiation(s). The fourth arrangement(s) can be further configured to generate at least one image of at least one portion of the sample(s) based on the data. The first arrangement(s) can include at least one section that is non-stationary, and/or which can include an optical waveguiding arrangement. At least one of the section(s) of the second arrangement(s) can be provided within a catheter. The fourth arrangement can be further configured to correct at least one portion of the image(s) based on at least one group of A-lines of (i) the second radiation, and/or (ii) the third radiation. The correction of the portion(s) of the image(s) can be performed for all of the A-lines.

In yet another exemplary embodiment of the present disclosure, the first portion(s) of the second arrangement(s) can be a first surface of the second arrangement(s), and the second portion(s) of the second arrangement(s) can be a second surface of the second arrangement(s). The first and second surfaces can be provided on or in a catheter, a handheld arrangement and/or a non-stationary arrangement. The fourth arrangement can determine at least two polarization states of the fourth radiation(s). The second arrangement can include two separate structures, one of the structures having a material that is different from that of another one of the structures.

These and other objects, features and advantages of the present disclosure will become apparent upon reading the following detailed description of embodiments of the disclosure, and the appended claims.

BRIEF DESCRIPTION OF THE DRAWINGS

Further objects, features and advantages of the present disclosure will become apparent from the following detailed description taken in conjunction with the accompanying drawings showing illustrative embodiments of the present disclosure, in which:

FIG. 7($b$) is an illustration of a single component of Stokes vector with narrow spectral window applied according to an exemplary embodiment of the present disclosure, with white circular lines indicate sheath positions;

FIGS. 9($c$) and 9($d$) are exemplary 3D plots on a Poincare sphere of the optic axis of a catheter sheath before and after, respectively, an application of the exemplary correction procedure shown in FIG. 8 is made;

FIG. 12($b$) is an illustration associated with data from the same frame for longitudinal optic axis, FIG. 12($c$) is an illustration associated with data from the same frame for retardation;

FIG. 12($d$) is an illustration associated with data from the same frame for circumferential optic axis;

FIG. 12($e$) is an illustration associated with data from the same frame for histology with H&E stain;

FIG. 12($f$) is an illustration associated with data from the same frame for comprehensive circumferential (axis multiplied with retardation and overlaid on structural data of FIG. 12($a$);

FIG. 13($a$) is a schematic diagram of the PS-OFDI system according to an exemplary embodiment of the present disclosure;

FIG. 13($b$) is a photograph of an exemplary optical rotary junction and endoscopic imaging probe according to the exemplary embodiment of the present disclosure with the illustrated rotary junction stage facilitating an exemplary pullback length of up to approximately 10 cm;

FIG. 13(c) is a schematic diagram of the sheath used with endoscopic probe made of the transparent polymer fluorinated ethylene propylene (FEP), e.g., with walls about 0.43 mm thick, according to an exemplary embodiment of the present disclosure;

FIG. 17(a) is an exemplary photograph of crossed rubber phantoms with the use of an exemplary endoscopic probe according to an exemplary embodiment of the present disclosure;

FIG. 17(b) is an illustration of an exemplary retardance of the phantoms;

FIG. 17(c) is an illustration of an exemplary corrected Q component of the OA for the phantoms;

FIG. 19(a) is an exemplary conceptual comparison between results provided by the linear filtering and the exemplary contour-adaptive filtering FIG. 19(b) is an illustration of 12 point linear filtering applied to the Stokes vectors in a frame imaged in a pig bronchus;

FIG. 19(c) is an illustration of the same data from as provided in FIG. 19(b), but filtered using a 12 point exemplary contour-adaptive filter;

FIGS. 19(d) and 19(e) are expanded exemplary regions from FIGS. 19(b) and 19(c) highlighting the impact of the tissue contour-adaptive filter;

FIG. 20(a) is a photograph of rubber phantom used for dimensions comparison, with the phantom measured to be 11.37+/−0.15 mm at its widest point and 3.25+/−0.15 mm at its narrowest;

FIG. 20(b) is an illustration of an exemplary circularization without refractive index compensation of OCT image acquired with endoscopic probe of the phantom in FIG. 20(a), with the measured diameters being, e.g., 3.35 mm and 10.90 mm;

FIG. 20(c) is an illustration of an exemplary circularization with refractive index compensation, with the measured diameters being 3.35 mm and 11.23 mm;

FIG. 20(d) is illustrations of an exemplary circularized image from swine bronchus without a refractive index compensation;

FIG. 20(e) is illustrations of an exemplary circularized image from swine bronchus with a refractive index compensation demonstrating the correction of discontinuities at mucus interfaces;

FIGS. 20(f) and 20(g) are exploded views of up of one of the mucus interfaces from frames shown in FIGS. 20(d) and 20(e);

FIG. 21(a) is an illustration of Photograph of an exemplary system according to a further exemplary embodiment of the present disclosure;

FIG. 21(b) is a schematic diagram of the exemplary system shown in FIG. 21(a);

FIG. 22(a) is an illustration of an exemplary volumetric reconstruction of a 2 cm and a pullback performed at a rate of 1 mm/s, cropped for clarity of the exemplary ASM in a bronchus of a healthy human volunteer visualized in vivo with fiber-based PS-OCT;

FIG. 22(b) is an illustration of a cross section from volumetric data shown in FIG. 23(a);

FIG. 22(c) shows exemplary results based on the same pullback from as provided in the results of FIG. 22(a) with the retardance plotted rather than the OA—in contrast with OA, retardance is a scalar quantity dependent on the density of ASM bundles;

FIG. 22(d) shows an illustration of a cross section from the data shown in FIG. 23(b) with a retardance plotted therein;

FIG. 23(a) is a PS-OCT image frame of a cross section of a canine bronchiole;

FIG. 23(b) is an illustration of a corresponding histology match, stained with alpha smooth muscle actin, and the slide being digitized at 5× magnification;

FIGS. 23(c) and (d) are PS-OCT image frame and matching histology, respectively, from a swine bronchiole, obtained in substantially the same manner as described for the canine match;

FIG. 25(e) is a graph of an exemplary absolute thickness profile from a 1.3 cm longitudinal cross section of the non-asthmatic bronchus (region indicated with dashed line in FIG. 25(b);

FIG. 25(f) is a graph of an exemplary thickness profile of the image shown in FIG. 25(e), divided by lumen perimeter measured at the corresponding longitudinal position;

FIGS. 25(g) and 25(h) are graphs of the same profiles for the asthmatic bronchus;

FIG. 25(i) is a graph of an exemplary airway perimeter as a function of pullback location for non-asthmatic; and FIG. 25(j) is a similar graph of the asthmatic airway;

Figure 1:
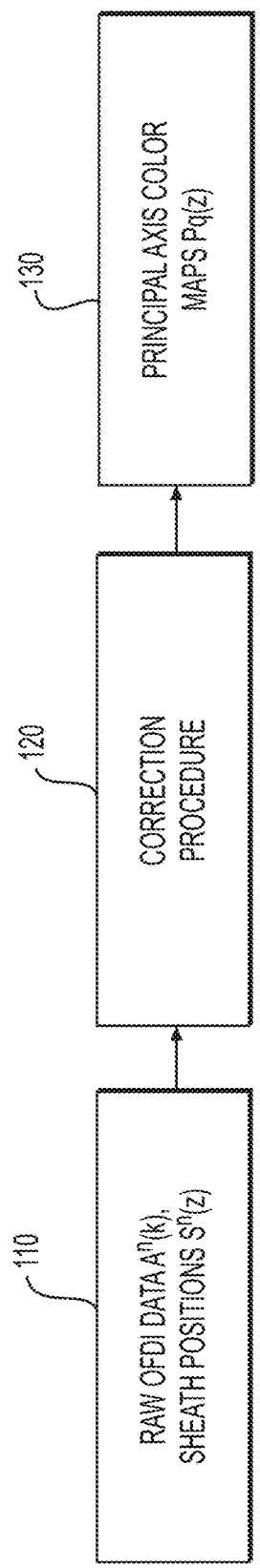
FIG. 1 is a flow diagram of a method for compensating for variation in the input polarization mode that occurs in a polarization-sensitive optical frequency domain imaging (PS-OFDI) system according to an exemplary embodiment of the present disclosure.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject disclosure and appended claims.

DETAILED DESCRIPTION OF EXEMPLARY EMBODIMENTS

FIG. 1 illustrates a flow diagram of a method for compensating for variation in the input polarization mode that occurs in a polarization-sensitive optical frequency domain imaging (PS-OFDI) system according to an exemplary embodiment of the present disclosure. For example, as shown in FIG. 1, a frame or frames of raw PS-OFDI data and user provided depth locations of the sheath boundaries across the frame can be provided as input 110 to the exemplary procedure according to an exemplary embodiment of the present disclosure. Such input is provided to the exemplary correction procedure 120. The output of such correction procedure can include a plurality of color-coded frames per input frame 130, which can represent the components of the optic axis of the tissue within the frame which are parallel and perpendicular to the optic axis of the sheath.

Figure 2:
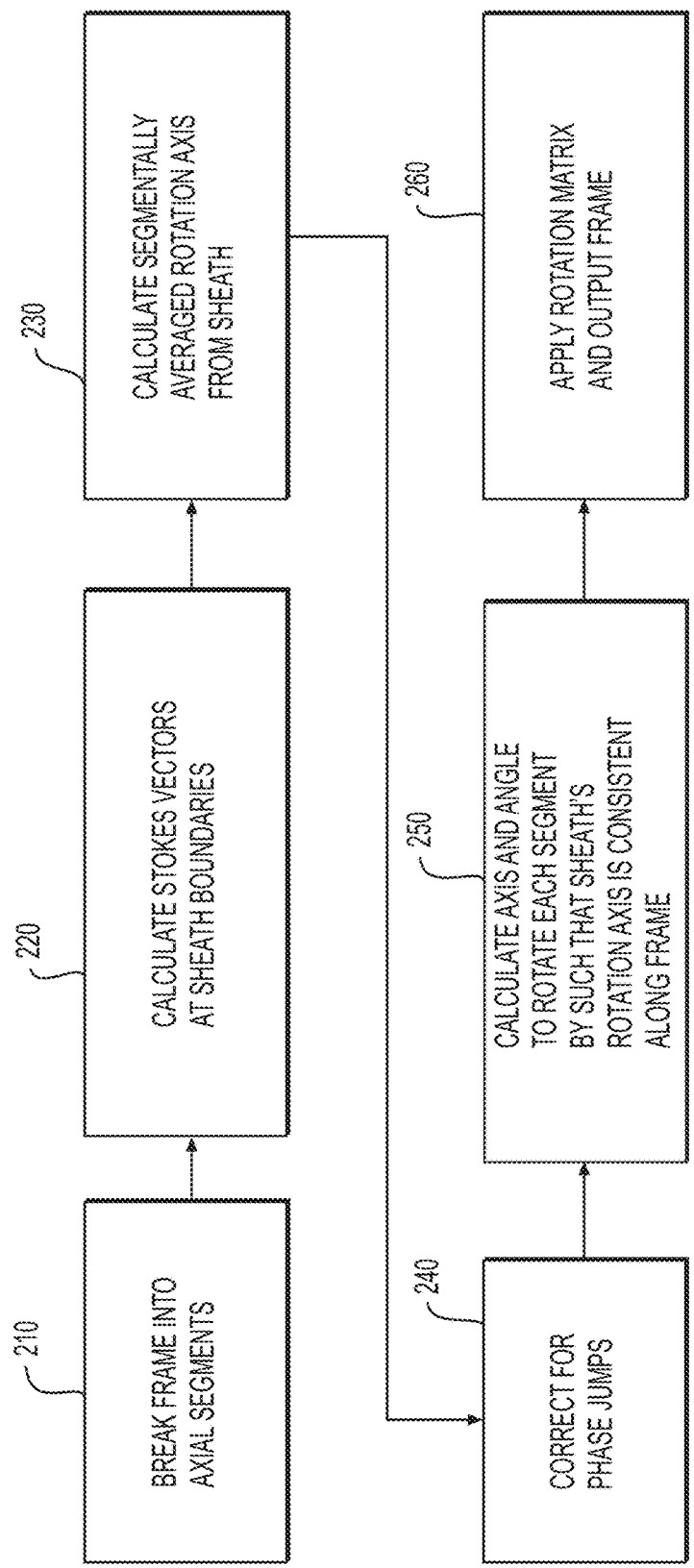
FIG. 2 is a flow diagram of a correction procedure for the method shown in FIG. 1 according to an exemplary embodiment of the present disclosure.

FIG. 2 shows a flow diagram of certain steps of the correction procedure of the method shown in FIG. 1 according to an exemplary embodiment of the present disclosure. For example, as shown in FIG. 2, in sub-procedure 210, a frame can be broken down into a number of separate axial segments, which can be composed of individual axial depth profiles (e.g., A-lines), with the number of which determined based on how quickly the polarization state changes within a frame. Then, in sub-procedure 220, the Stokes vectors can be calculated at the sheath boundaries for each A-line. In sub-procedure 230, the measured optic axis of the sheath at a given A-line can be calculated based on the values of the Stokes vectors at the boundaries of the sheath, and averaged per axial segment. Further, in sub-procedure 240. The measured axis is phase unwrapped when a shift of greater than it can be detected from one axial segment to another (e.g., to correct for phase jumps). Then, in sub-procedure 250, a rotation matrix for rotating each axial segment to a common axis can be calculated (e.g., such that sheath's rotation axis is consistent along frame). The direction and magnitude of this rotation can be determined by, e.g., an application of exemplary vector mathematics known to those having ordinary skill in the art. Further, in sub-procedure 260, the rotation matrix can be applied and the results can be outputted.

Figure 3:
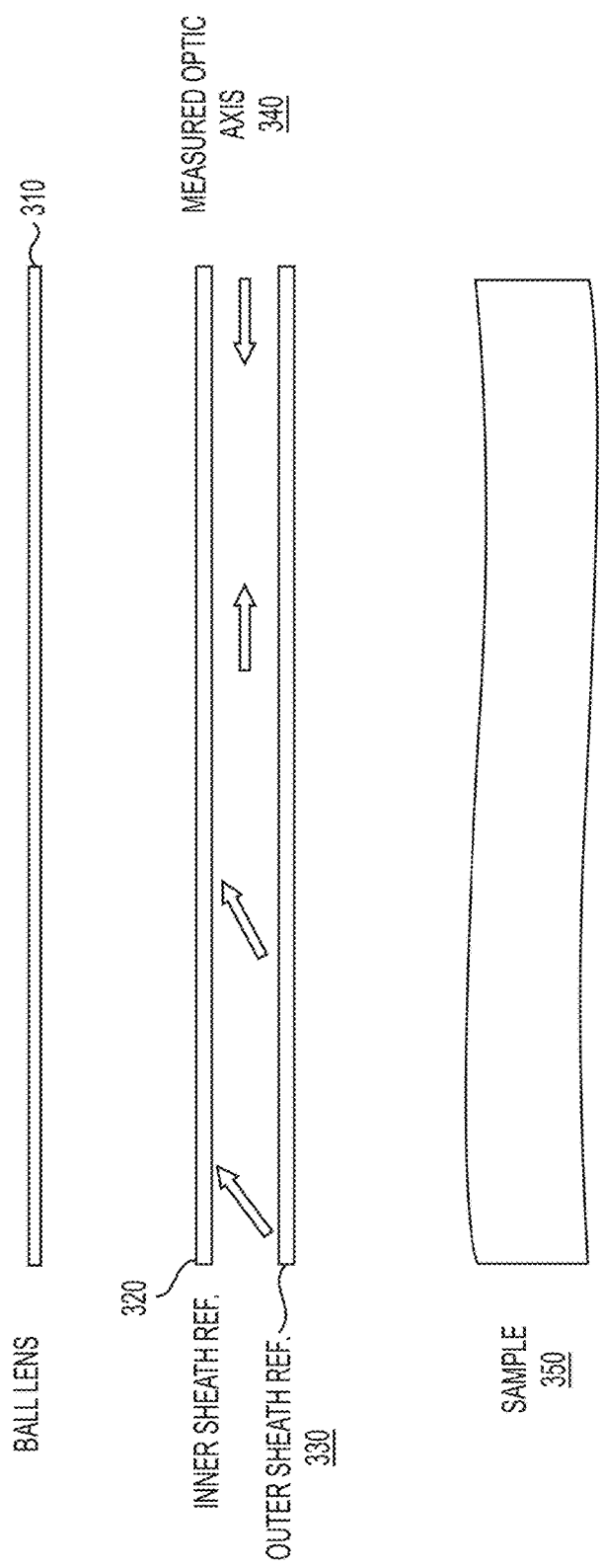
FIG. 3 is a side view of an exemplary configuration and radiation transmission diagram during a measurement of an optical axis of the tissue, according to an exemplary embodiment of the present disclosure.

FIG. 3 illustrates a side view of an exemplary configuration and radiation transmission diagram during a measurement of an optical axis of the transmission by applying the exemplary correction procedure, according to an exemplary embodiment of the present disclosure. In particular, as shown in FIG. 3, each frame can include exemplary imaging of the ball lens 310 of the catheter, inner and outer sheaths 320, 330 of the catheter, and the sample 350 itself. For example, when calculating an optic axis of the sheath, which can be the material of which is almost transparent yet possesses at least some birefringence, such measured axis 340 varies across the frame, e.g., in a substantially the same way a measured optic axis 340 of the sheath and/or of the tissue.

Figure 4:
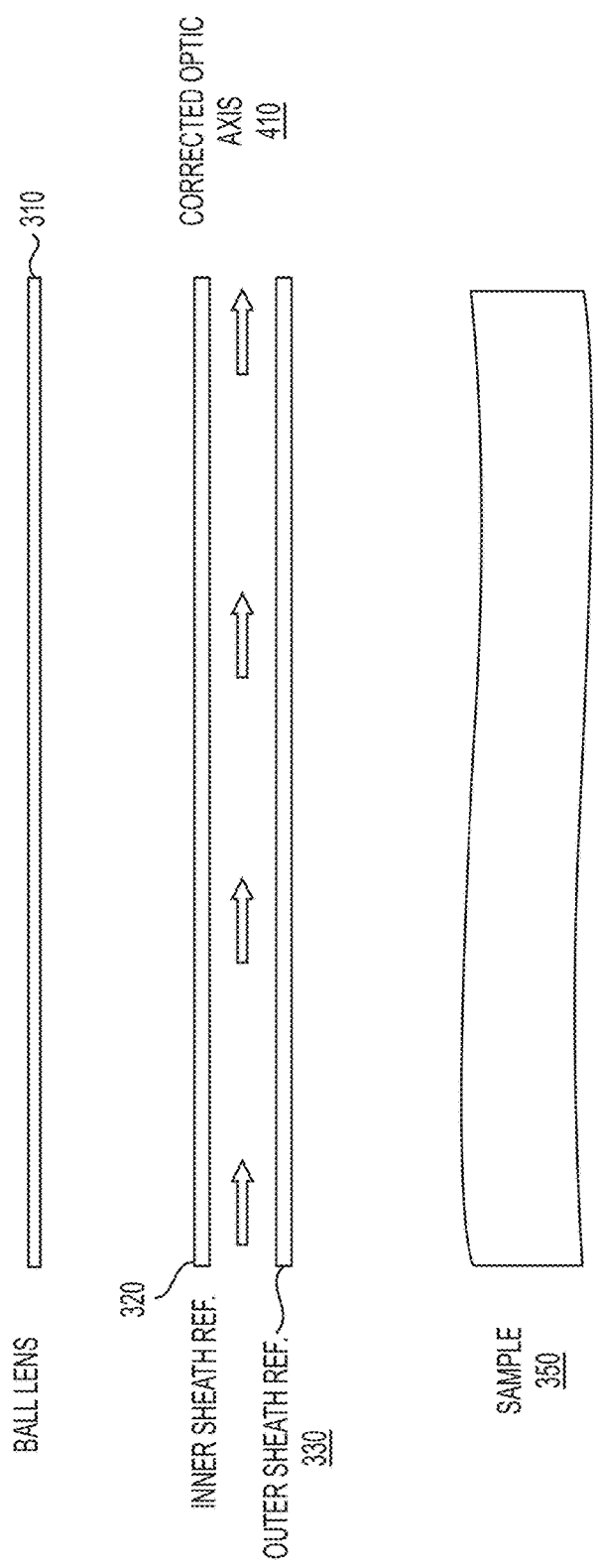
FIG. 4 is a side view of the exemplary configuration of FIG. 3 and of a radiation transmission diagram upon a correction of the optical axis of the tissue according to the exemplary embodiment of the present disclosure.

FIG. 4 shows a side view of the exemplary configuration of FIG. 3 and of a radiation transmission diagram upon a correction of the optical axis of the tissue after the application of the exemplary correction procedure, according to the exemplary embodiment of the present disclosure. As shown in FIG. 4, the measured optic axis of the sheath is corrected to form a corrected optical axis 410, which (due to such correction) is consistent across the frame. As a result, substantially the same consistency can be exhibited in the measurements of the principal axes within the tissue of the sample 350 itself, for the cases in which the measured principal axes of the tissue are either parallel or perpendicular to that of the sheath.

Figure 5:
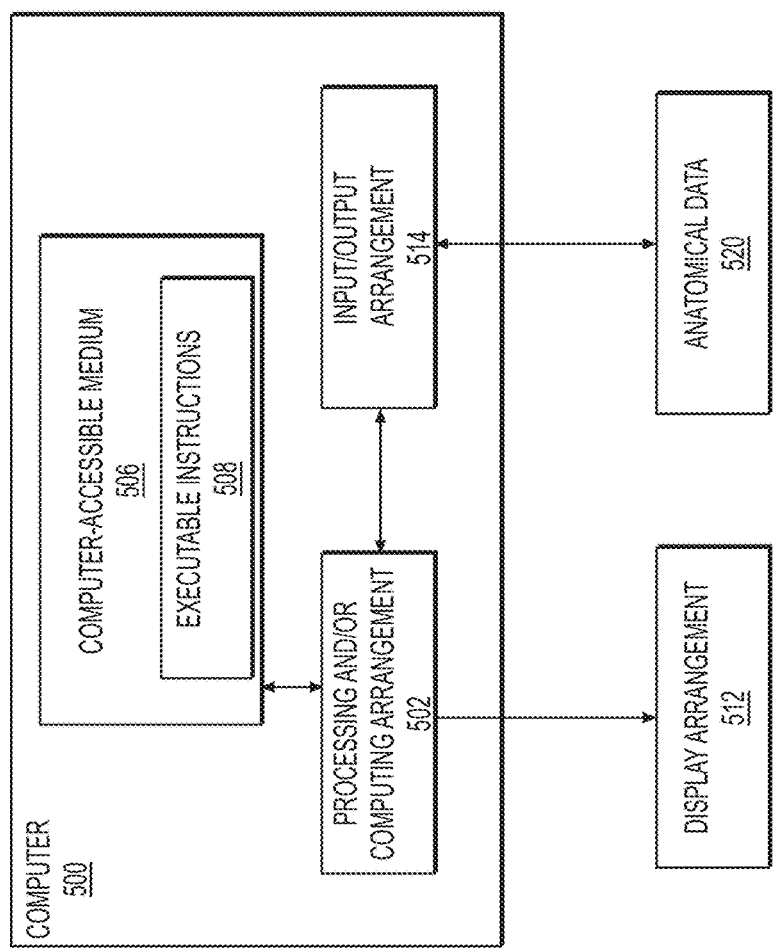
FIG. 5 a block diagram of a system according to the exemplary embodiment of the present disclosure.
Figure 6:
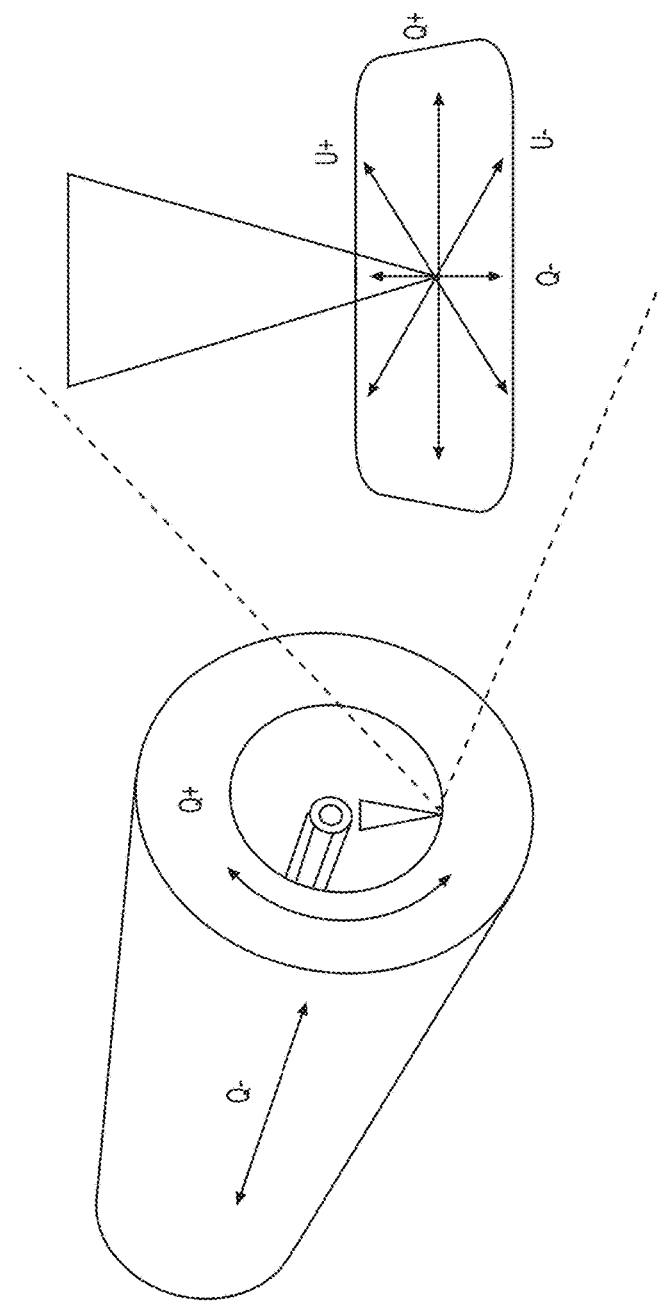
FIG. 6 is a schematic diagram indicating an orientation of the Stokes Parameters Q and U in a sample frame.

FIG. 5 shows a block diagram of an exemplary embodiment of a system according to the present disclosure, which can implement the exemplary embodiments of the method and procedures described herein. For example, exemplary procedures in accordance with the present disclosure described herein can be performed by a processing arrangement and/or a computing arrangement 502. Such processing/computing arrangement 502 can be, for example, entirely or a part of, or include, but not limited to, a computer/processor 504 that can include, for example, one or more microprocessors, and use instructions stored on a computer-accessible medium (e.g., RAM, ROM, hard drive, or other storage device).

As shown in FIG. 5, for example, a computer-accessible medium 506 (e.g., as described herein above, a storage device such as a hard disk, floppy disk, memory stick, CD-ROM, RAM, ROM, etc., or a collection thereof) can be provided (e.g., in communication with the processing arrangement 502). The computer-accessible medium 506 can contain executable instructions 908 thereon. In addition or alternatively, a storage arrangement 510 can be provided separately from the computer-accessible medium 506, which can provide the instructions to the processing arrangement 502 so as to configure the processing arrangement to execute certain exemplary procedures, processes and methods, as described herein above, for example.

Further, the exemplary processing arrangement 502 can be provided with or include an input/output arrangement 514, which can include, for example, a wired network, a wireless network, the internet, an intranet, a data collection probe, a sensor, etc. For example, anatomical data 520 can be provided to the input/output arrangement 514. As shown in FIG. 5, the exemplary processing arrangement 502 can be in communication with an exemplary display arrangement 512, which, according to certain exemplary embodiments of the present disclosure, can be a touch-screen configured for inputting information to the processing arrangement in addition to outputting information from the processing arrangement, for example. Further, the exemplary display 512 and/or a storage arrangement 510 can be used to display and/or store data in a user-accessible format and/or user-readable format.

Figure 7B:
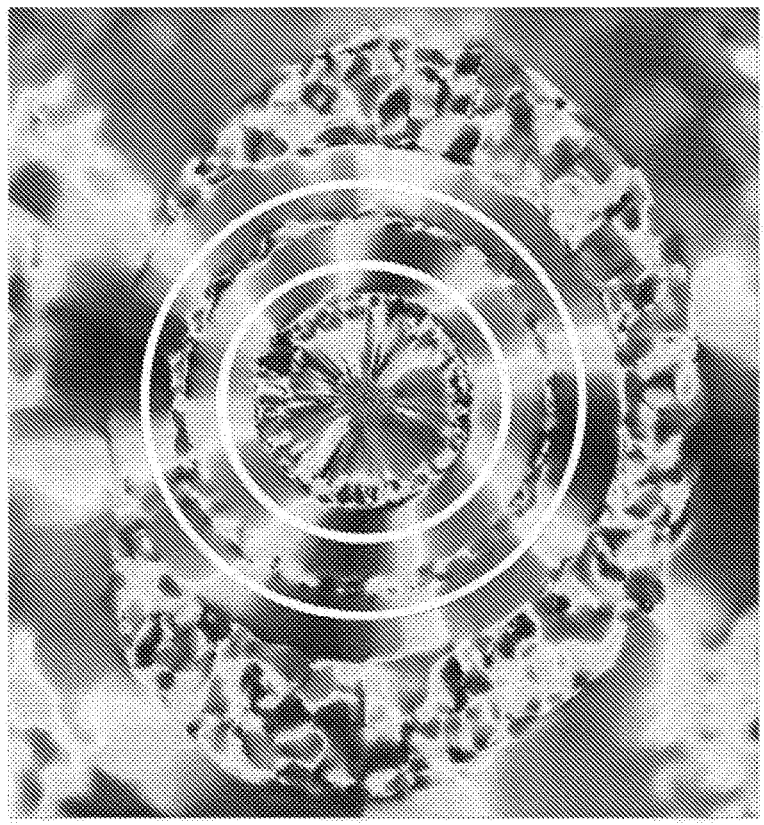
FIG. 7($a$) is an exemplary structural image of a catheter sheath according to an exemplary embodiment of the present disclosure during in vivo imaging.
Figure 7A:
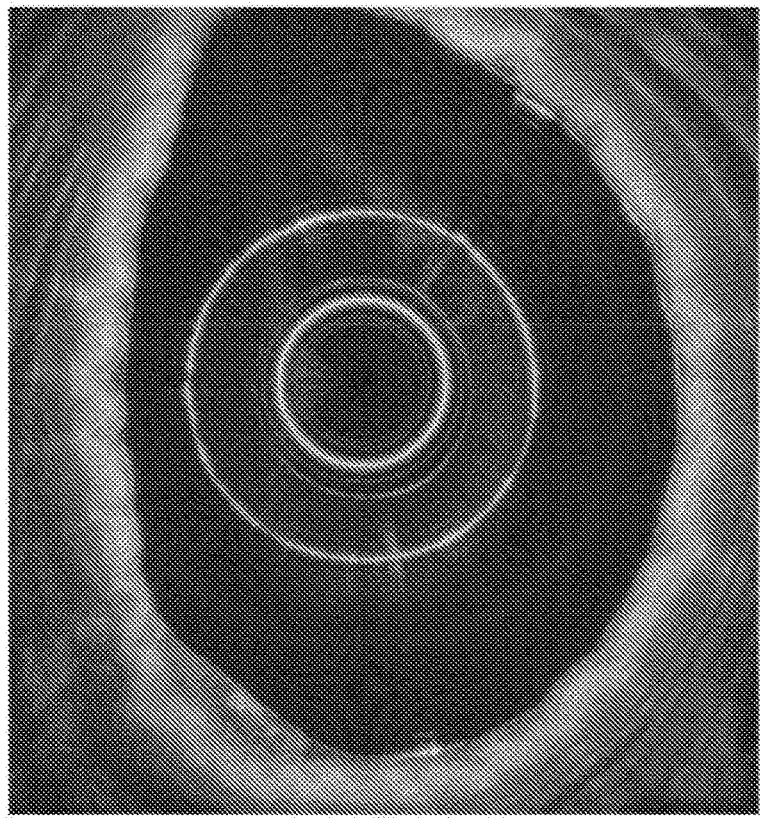

According to a further exemplary embodiment of the apparatus and method according to the present disclosure, to extract useful information from the sheath, the optic axis of the sheath can initially be determined. Since the exemplary sheath itself can be nearly transparent, an exemplary determination of the birefringence from reflections inside the sheath may be difficult. Instead, signals reflected from the inner and outer surfaces of the sheath can be used, according to an exemplary variant of the present disclosure. Furthermore, a polarization mode dispersion (PMD) can give rise to depth-varying measurements for the optic axis of a single reflector, which can cause significant aberrations in subsequent correction calculations. In order to mitigate the effect of PMD in the determinations, a narrow spectral window at the center of the detection spectrum can be employed, e.g., similar to the technique devised in, e.g., Ref. 3. Using a single narrow spectral window can have a dual advantage of eliminating the problem of PMD and making the axial locations of the reflections from the sheath easier identify and automatically locate, since using a narrow spectrum significantly reduces the axial resolution of the Fourier transform—obtained sample profile. An example of such a windowed measurement is depicted in FIG. 7(b), where the colormap represents measured values for only one of the (uncorrected) Stokes components. The positions of the inner and outer surfaces of the sheath are indicated with white lines. The corresponding exemplary structural image is provided for reference shown in FIG. 7(a).

Figure 8:
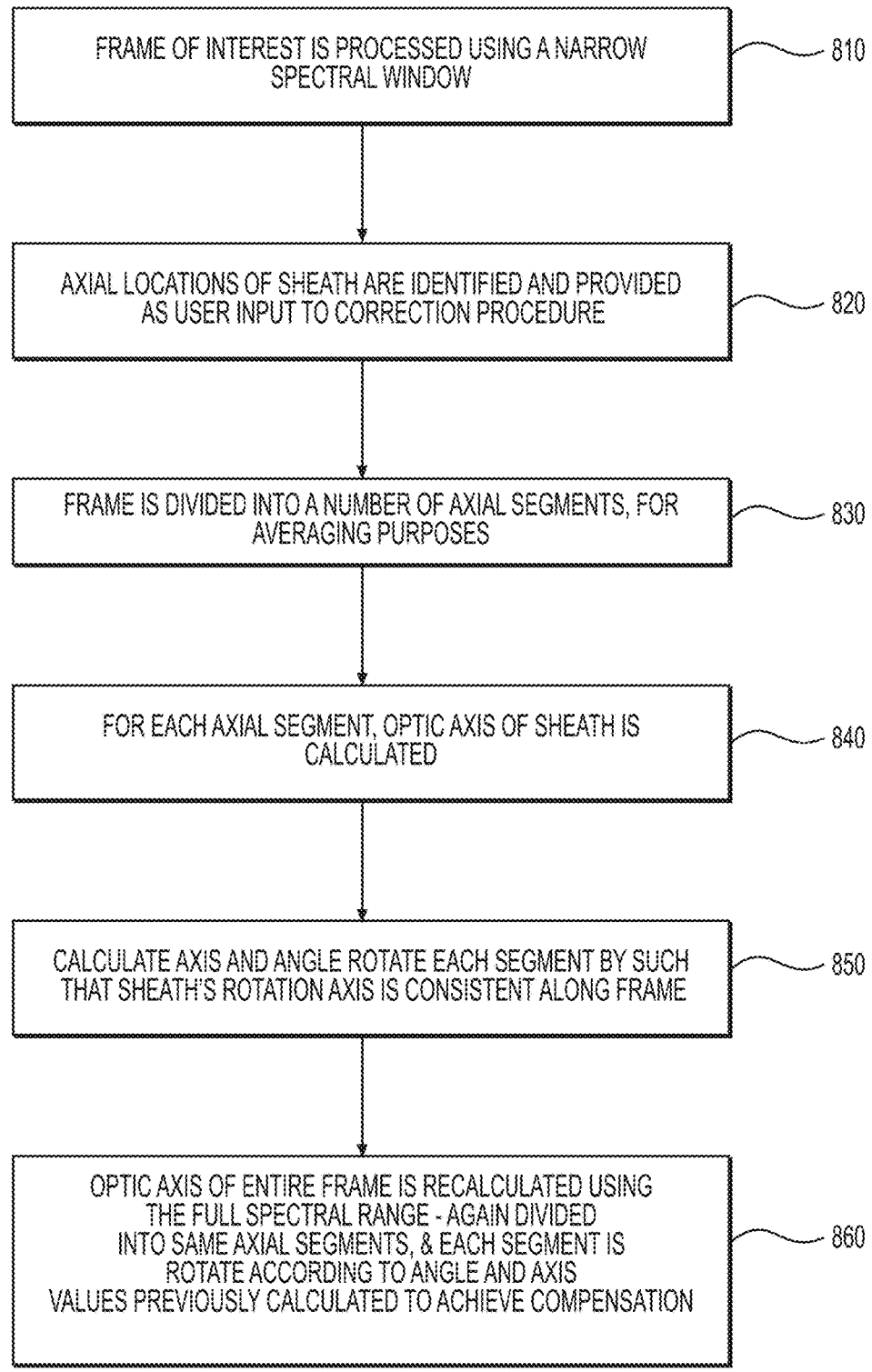
FIG. 8 is a flow diagram of an orientation correction procedure according to another exemplary embodiment of the present disclosure.

According to still another exemplary embodiment of the present disclosure, an exemplary procedure can be provided for obtaining an orientation correction. The exemplary procedure steps can be as follows, and shown in FIG. 8:

a) The frame of interest is processed as known in the art, with a possible exception that a narrow spectral window can be used (step 810).
b) The axial locations of the sheath are identified and provided as user input to the correction algorithm (step 820).
c) The frame is divided into a number of axial segments, for averaging purposes (step 830). As an example, for a frame including 1024 lateral polarization measurements, segments with a lateral width of 128 points were experimentally determined to be preferred. In general, the width is determined by the rate at which $J_{out}$ shifts over the course of a rotation.
d) For each axial segment, the optic axis of the sheath is calculated using the technique described earlier (step 840).
e) The angle and axis of rotation between the measured optic axis of the sheath at each axial segment and that of a common axis, identified as being the circumferential axis of the sheath as earlier described, are calculated (step 850).
f) $\pi$ phase jumps sometimes occur at or near on-axis alignments. These are corrected for by ensuring continuity of measurements within a $\pi/2$ tolerance.
g) The optic axis of the entire frame is recalculated using the full spectral range, but again divided into the same axial segments. Each segment is rotate according to the angle and axis values previously calculated in order to achieve compensation (step 860).

Prior to the exemplary application of the above-described exemplary procedure to the data, the measured optic axis of both the sheath and the sample can assume any value on the Poincare sphere—the volume spanned by the Stokes vector components. Because the optic axis of the sheath is oriented circumferentially, this exemplary procedure can correctly identify the Q components of the sample orientation, leaving the U-V plane indeterminate. Since the Q axis can correspond to both circumferential (positive Q) and longitudinal (negative Q) orientations, birefringent tissue with its optic axis orientated either circumferentially or longitudinally can be completely specified, while partial alignment to one of the two orientations ways that likely the Q component is accurately identified, with the U component remaining unknown (since circular orientation cannot be detected, the necessity of the V component to be null offers a second condition). A possible situation in which little or no information is gained is can be the one in which the optic axis of the birefringent tissue is oriented, e.g., entirely along the U axis.

Figure 9A:
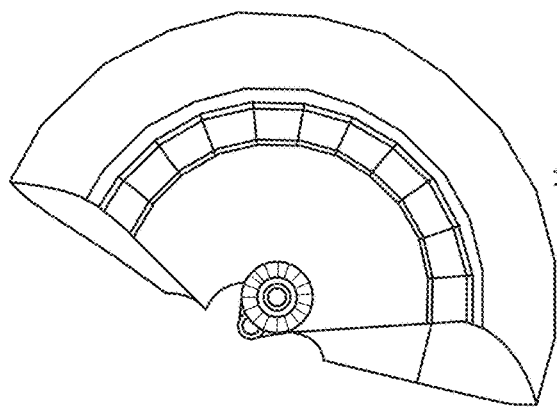
FIGS. 9($a$) and 9($b$) are illustration of before and after, respectively, an application of the exemplary correction procedure shown in FIG. 8 is made.
Figure 9B:
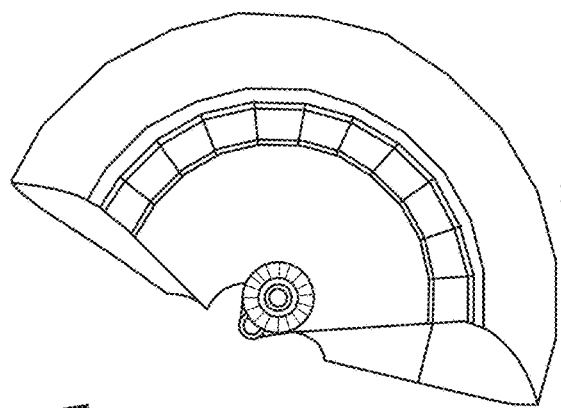
Figure 9C:
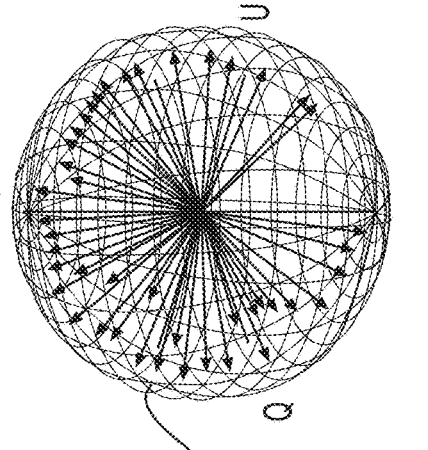
Figure 9D:
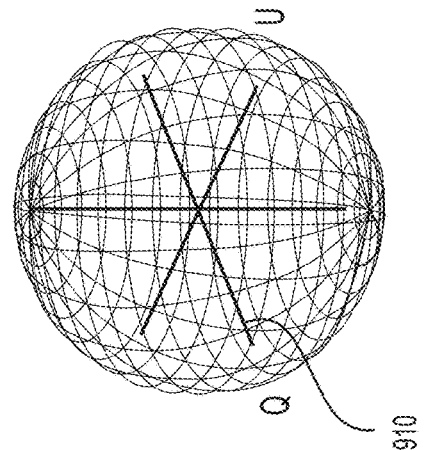

FIGS. 9(a)-9(d) are provided to clarify an exemplary overall effect of the exemplary procedure. For example, FIGS. 9(a) and 9(b) are illustration of before and after situations, respectively, with the colors intended to serve as a simplified representation of the optic axis orientation for the sheath and for orthogonally oriented birefringence tissue components. FIGS. 9(c) and (d) show exemplary 3D graphs on a Poincare sphere of the optic axis of the exemplary catheter sheath, acquired from experimental data. Each of the vectors 910 can represent a measurement of the sheath's optic axis at an A-line segment along a single frame. As described herein, the exemplary measured orientation of the optic axis can vary considerably over the course of a single rotation. After the correction procedure is applied, each measurement can be rotated so that they all lie along the same direction (+Q).

Figure 10:
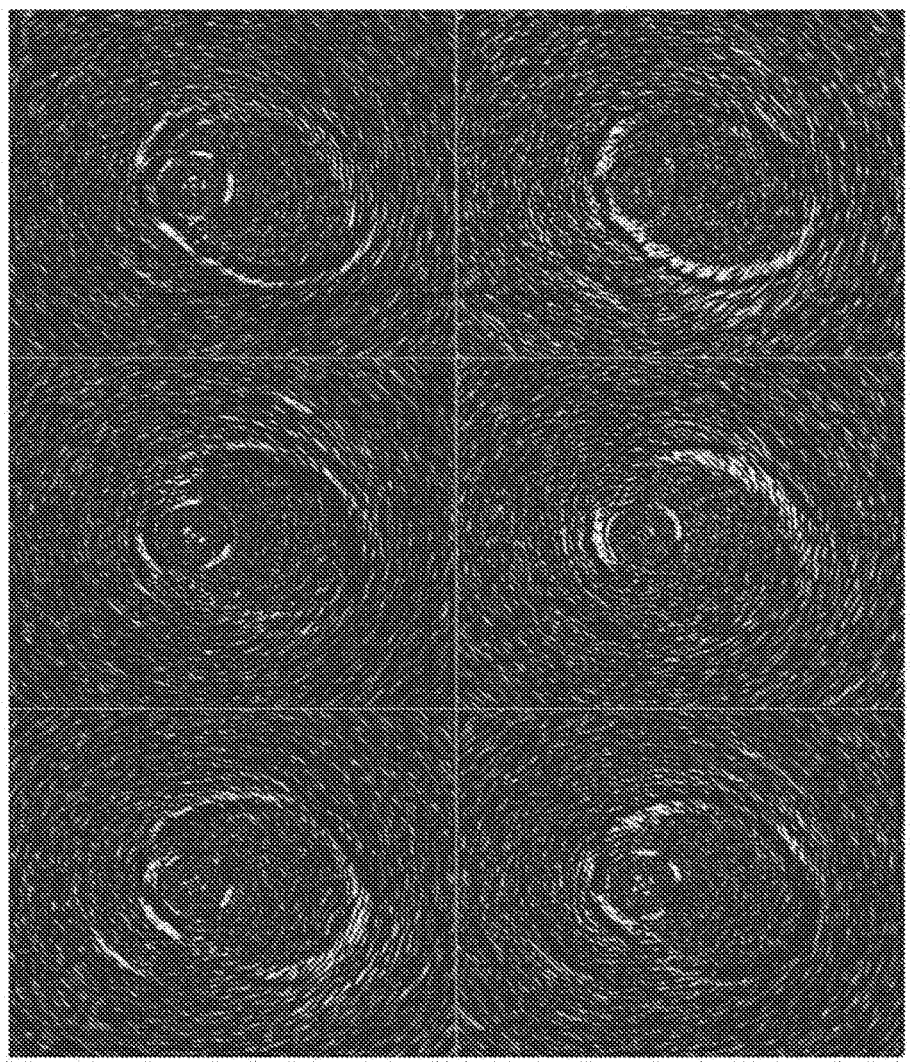
FIG. 10 is an illustration of six exemplary frames representing six uncorrected components taken from measurements of a swine bronchiole.

FIG. 10 shows exemplary optic axis measurements acquired during an exemplary catheter imaging of a swine bronchiole. The six frames of Figure correspond to the six optic axis components (+/−Q, +/−U, +/−V) as measured in the detection arm of the system. The exemplary results can be compared with those of FIG. 5, which represent the six components after the correction algorithm has been applied. The top two frames of FIG. 11 belong to the corrected axis circumferential (+Q) on the left and longitudinal (−Q) on the right. The remaining four frames of FIG. 11 can involve a mismatch of the unresolved components, and are largely devoid of any sample signal. In the top two frames structure that was indistinct in the previous figure becomes apparent.

Figure 11:
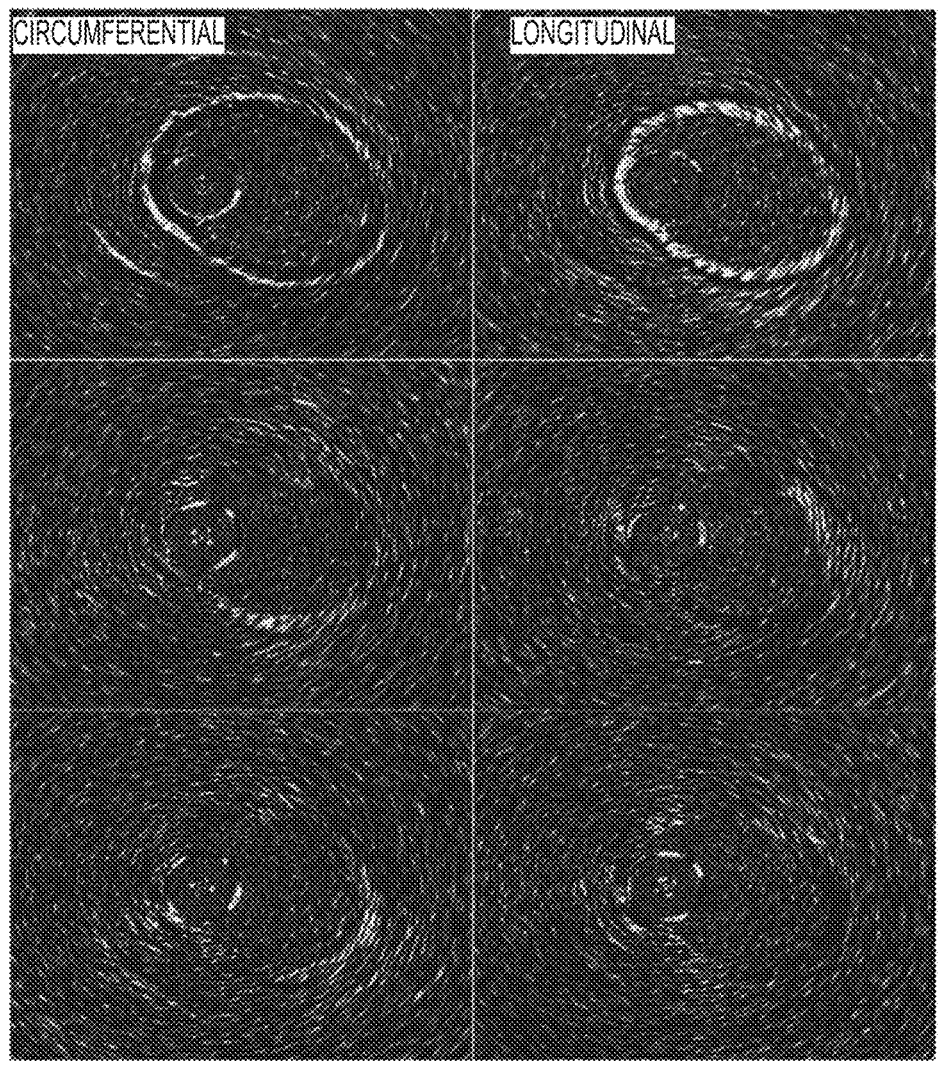
FIG. 11 is an illustration of data provided in FIG. 10 post-correction, with the corrected components (e.g., circumferential and longitudinal, belonging to +/−Q) are located in the top row.
Figure 12A:
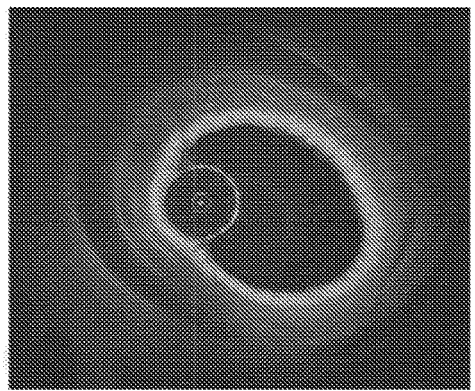
FIG. 12($a$) an illustration associated with data from the same frame for Structural OFDI.
Figure 12B:
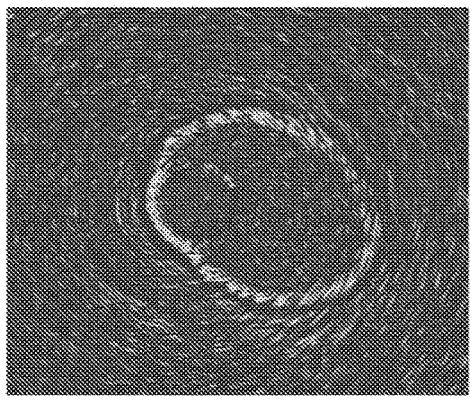
Figure 12C:
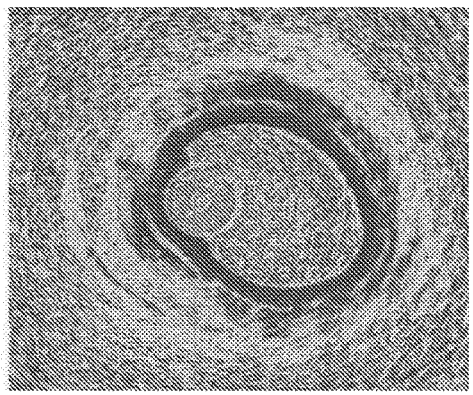
Figure 12D:
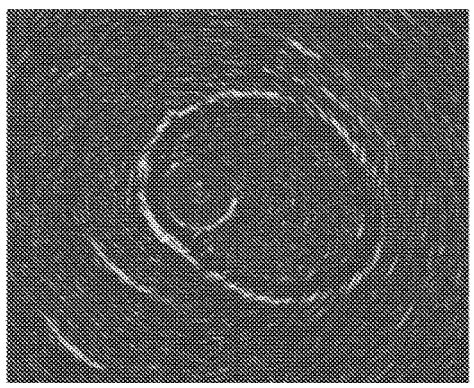
Figure 12E:
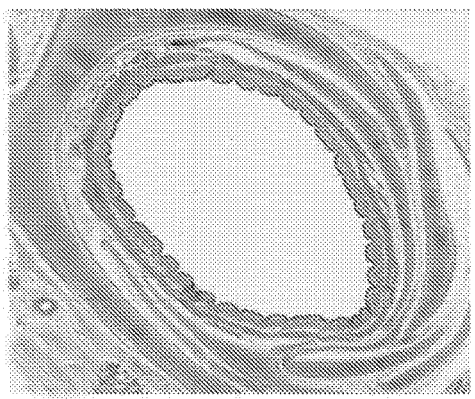
Figure 12F:
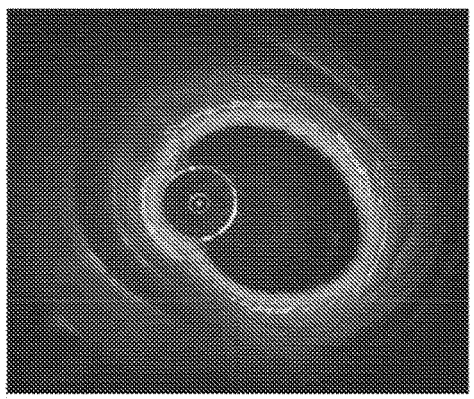
Figure 14B:
FIG. 14(b) is an in-plane (circumferential) OA selecting the trachealis muscle.
Figure 14D:
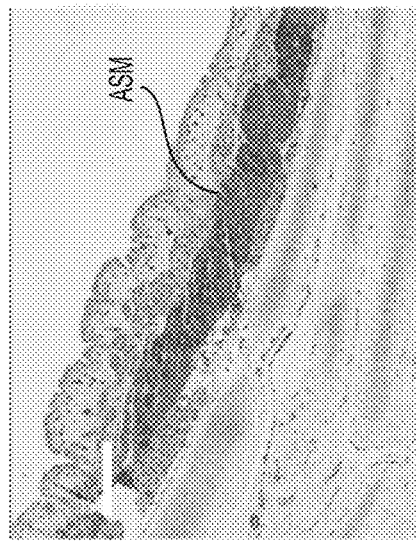
FIG. 14(d) is an illustration of □SM-actin stain highlighting the trachealis muscle; Scale bars, 500 μm.
Figure 14A:
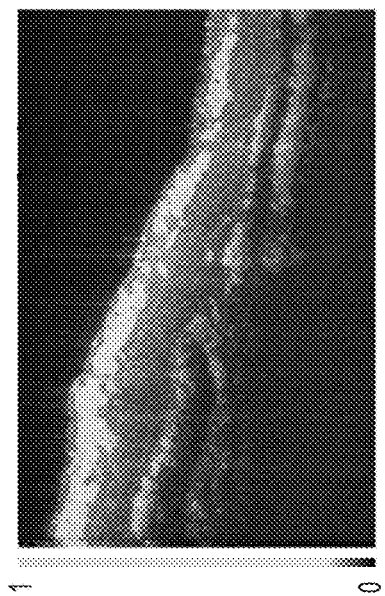
FIG. 14(a) is an illustration of an out of plane (longitudinal) component of the OA selecting the lamina propria as well as some of the perichondria.
Figure 14C:
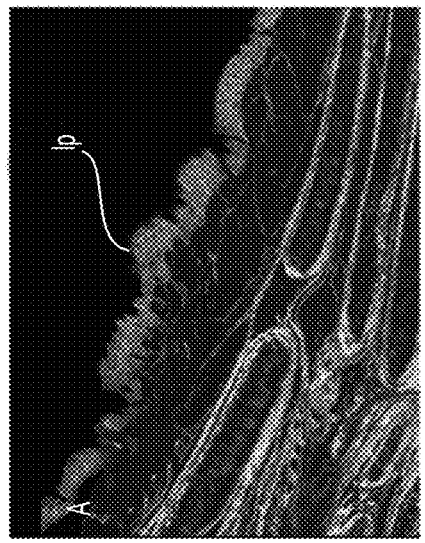
FIG. 14(c) is an exemplary histology slide imaged with a polarized light microscope highlighting the lamina propria.
Figure 15A:
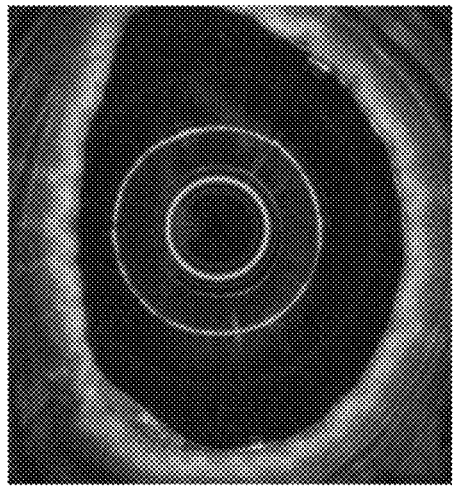
FIG. 15(a) is an illustration of an exemplary endoscopic sheath in a circularized structural image according to an exemplary embodiment of the present disclosure.
Figure 15B:
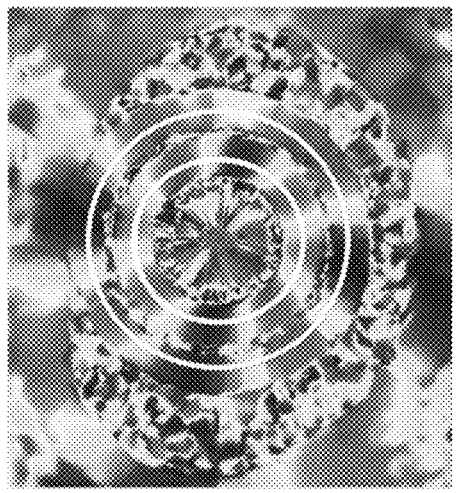
FIG. 15(b) is an illustration of an exemplary component of the Stokes vector plotted in the same frame and location as illustrated in FIG. 15(a), e.g., with a narrow (100 point), centered spectral window being used for the Stokes calculation.
Figures 15C, 15D:
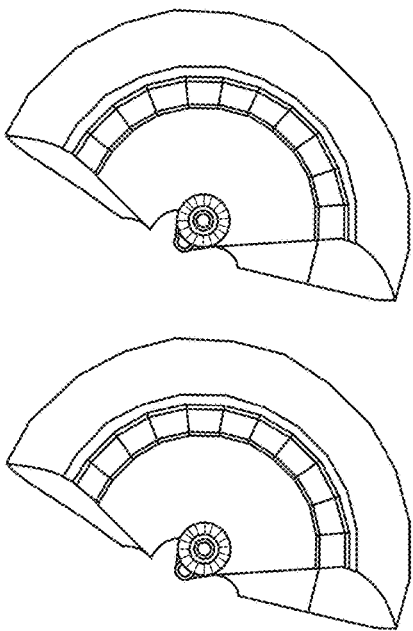
FIGS. 15(c) and 15(d) are exemplary depictions of OA correction before the correction (Figure (c)) and after the correction (FIG. 15(d))
Figure 15E:
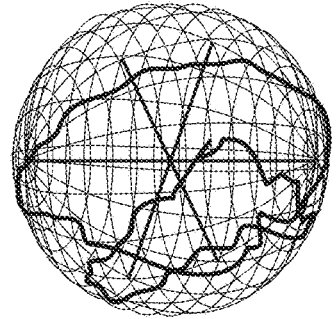
FIG. 15(e) is an illustration of an exemplary measured OA of the sheath before correction, plotted on the Poincare sphere.
Figure 15F:
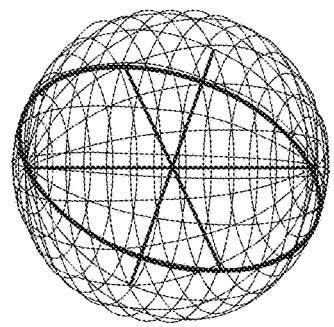
FIG. 15(f) is an illustration of an axis for rotating an exemplary measured OA to corrected OA.
Figure 15G:
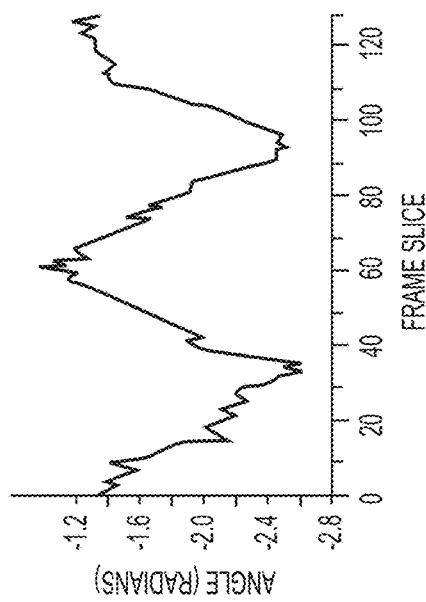
FIG. 15(g) is an illustration of a graph providing an angle for rotating the measured OA to corrected OA.
Figure 16A:
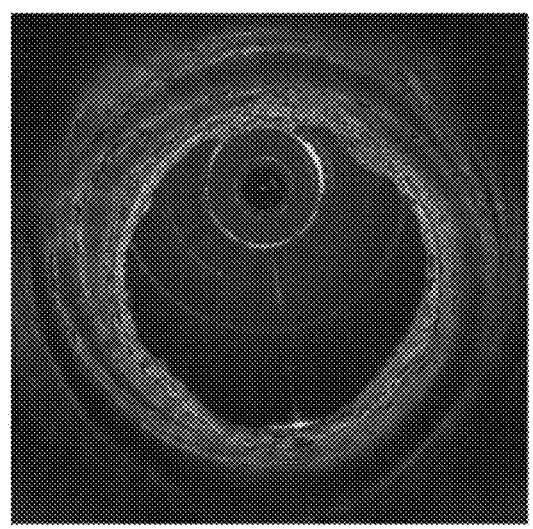
FIGS. 16(a)-16(c) are illustration of uncorrected OA components (+/−Q, U, and V shown in FIG. 6) from a swine bronchus.
Figure 16B:
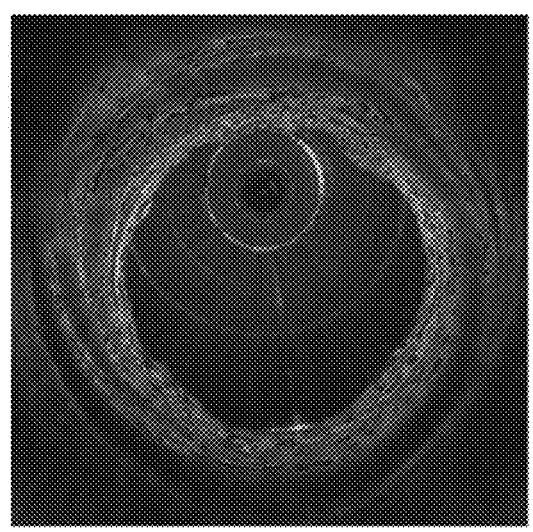
Figure 16C:
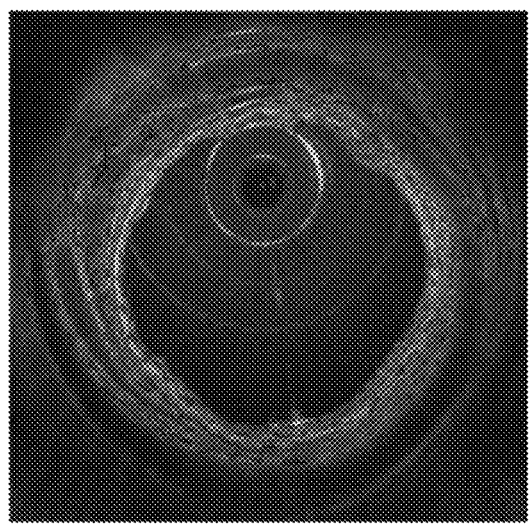
Figure 18A:
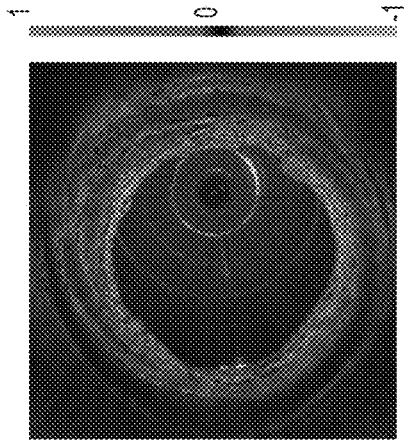
FIG. 18(a) is an illustration of a circumferential component of the corrected OA after correction thereof from FIGS. 16(a)-16(c)
Figure 18B:
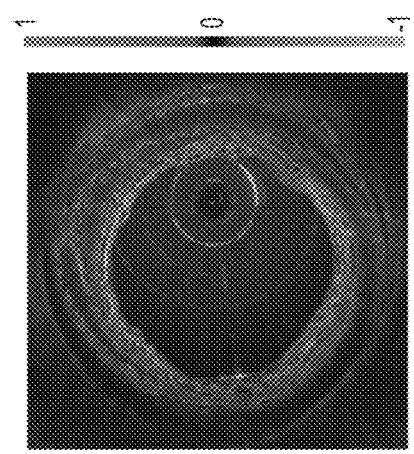
FIG. 18(b) is an illustration of an exemplary longitudinal component of the corrected OA.
Figure 18C:
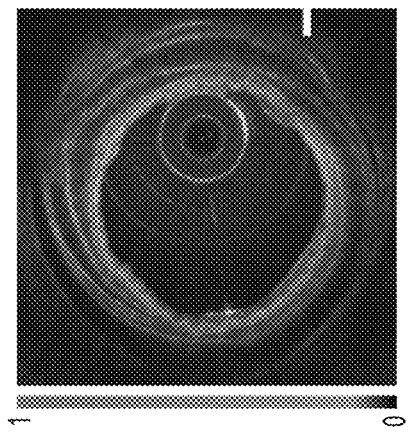
FIGS. 18(c) and 18(d) are illustration of further axes after the exemplary correction.
Figure 18D:
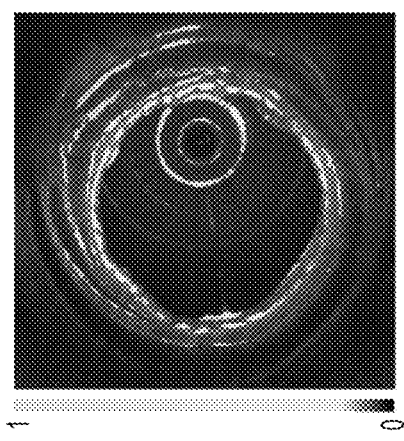

FIGS. 12(a)-12(f) illustrate images associated with data from the same frame as provided in FIGS. 10 and 11. In FIGS. 12(a)-12(f), exemplary relevant data can be included to assist contextualize the results of FIGS. 10 and 11, including the structural OFDI image, the retardation colormap, and the corresponding histology (H&E stain). For example, the last frame can be the exemplary circumferential axis data (shown in FIG. 12(d)) multiplied by the retardation data (shown in FIG. 12(c)) and overlaid on the structural data (shown in FIG. 12(a)), providing a comprehensive view of the circumferential component of the birefringent tissue.

Implementation of Exemplary PS-OCT System

Data was obtained using an exemplary PS-OFDI system as shown in FIGS. 13(a)-13(c). The exemplary system utilized a wavelength-swept laser 1310 (e.g., which can be centered at 1310 nm, FWHM of 120 nm) and include a semiconductor optical amplifier (e.g., made by Covega Corp.) and a spinning polygon mirror (e.g., which can operate at about 68 KHz) which served as a wavelength filter (e.g., made by Lincoln Laser Corp.). In particular, electromagnetic radiation (e.g., light) is provided from the wavelength-swept laser source 1310 which passes through a polarization controller 1312, a lens, an electro-optical modulator (EOM) 1315 (Newport Corp.) and another lens, to reach a beam splitter or a circulator (e.g., rotary splitter or fiber coupler) 1320. The electro-optic modulator 1315 (Newport Corp.) performs intra-A-line modulation of the polarization mode of the laser pulse between states orthogonal on the Poincare sphere. A splitter or fiber circulator 1330 further provides the signal to a reference arm 1340 (e.g., about 10%), containing, e.g., a fixed reflector (e.g., reference mirror) 1340 as well as an acousto-optic modulator 1350 (Brimrose Corp.) so as to generate a reference signal/radiation. The reference light/radiation is sent back to the splitter 1330 which passes the light/signal to a polarization controller.

In the sample arm, either a bench-top microscope or an endoscopic probe 1326 were connected through a rotary optical junction Rj 1324, which joined the fixed fiber of the system to (in the case of endoscopic probe 1326) the rotating fiber of the probe 1326. The signals/light/radiation from the sample arm is provided back from the endoscopic probe 1326 to the splitter 1322, which then forward such signals/light/radiation to a beam splitter (BS) to be combined with the reference signal/radiation, which the provides the combined (e.g., interfered) interfered signals to balanced photodetectors 1362, 1364 (New Focus Corp.). The electrical signals from the photodetectors can be digitized using a 14-bit (CONFIRM) dual-channel 170 MS/s data acquisition board (Signatec Inc.)—A/D, and then the results can be provide the CPU for processing. Using this exemplary configuration, it is possible to achieve a ranging depth (in air) of about 9.77 mm and obtained about 2048 A-lines per frame at a rate of 33.2 frames per second. The number of points obtained per A-line was about 2248. The pixel depth resolution in tissue was about 4.5 μm and the frame pitch was about 15 μm in endoscopic imaging using a pullback rate of about 0.5 mm/s (30 μm at 1 mm/s).

Exemplary Raw Data Processing

Structural Images. Structural images were obtained via, e.g., fast Fourier transform (FFT) of the background-subtracted raw data. Depth degeneracy was eliminated by, e.g., re-centering to DC and zeroing the negative-depth portion of the data. Dispersion compensation and mapping to linear k-space were achieved mathematically [see, e.g., Ref 30]. The final images were about 2048×2048 pixels in size and displayed on a logarithmic (dB) scale.

PS Images. Polarization sensitivity limited to the Q-U plane was achieved using, e.g., a two polarization state input approach [see, e.g., Ref 31]. In this exemplary manner, orthogonal (on the Poincare sphere) polarization states from adjacent A-lines are converted to a Stokes representation and used to calculate the local retardance and optic axis (OA) of the sample according to the exemplary equations:

$$OA = (S_1(z+dz) - S_1(z)) \times (S_2(z+dz) - S_2(z)) \qquad (1)$$

$$\theta = \arccos\left(\frac{(S_1(z+dz) \times PA) \cdot (S_1(z) \times PA)}{|S_1(z+dz) \times PA||S_1(z+dz) \times PA|}\right) \qquad (2)$$

Where z is the depth of the pixel and dz (chosen to be 4 pixels, or ~18 μm in tissue) is the pixel interval used in the differential calculation. Using this technique the surface of the sample being imaged serves as the initial reference point. The detrimental effects of polarization mode dispersion (PMD) [see, e.g., Ref 32] were reduced by employing, e.g., a nine-window spectral binning procedure.

Exemplary Thresholding and Weighting. The birefringence data was both thresholded and weighted. First, birefringence was zeroed at pixel locations corresponding to pixels in the structural data that were at or below the structural noise floor. This value was determined by calculating the mean in a 80×80 pixel area outside of the sample region. This was done in order to mitigate the impact of specious birefringence in signal-poor regions. In addition to the structural thresholding, an exemplary step was introduced to the spectral binning algorithm for the weighting of the birefringence data. This exemplary step involved calculating the spread of the OA vectors across bins for each pixel and multiplying the pixel by the normalized correlation value.

Exemplary Separation of Optic Axis

With standard fiber-based PS-OFDI measurements, obtaining information about the OA of the sample may not be straightforward. Due to the innate, e.g., random birefringence associated with single mode fiber (SMF), the polarization state at the detectors can be generally different from that returned from the sample. When performing imaging using an exemplary microscope setup, this effect can be accounted for, e.g., by calibrating the system beforehand, as any or most calibrations performed can be consistent so long as the fibers are not disturbed. Using this exemplary approach to separate the in-plane and out-of-plane components of the OA in imaged pig trachea the smooth muscle can be oriented, e.g., approximately or specifically perpendicular to elastic fibers in the lamina propria, as shown in FIGS. 14(a)-14(d).

When using an optical rotary junction to rotate the imaging probe in endoscopic imaging, the measured polarization state is distorted even within a single imaging frame, due to the rotation of the imaging fiber itself. As a result, a birefringent element with a fixed orientation along the circumference of a cross-section of tissue have an OA that varies along said cross-section, as shown in FIGS. 15(a)-15(g). For example, white lines in FIG. 15(b) indicate sheath positions as located by the exemplary detection procedure. To compensate for this, exemplary system and method can be used to obtain at least a partial OA identification, e.g., in an endoscopic imaging configuration. This exemplary method utilizes that the catheter sheath, as shown in FIG.

13(c) possesses a moderate amount of birefringence (~0.43 µm/deg) along its axis of extrusion, that is, along the length of the sheath.

It is therefore possible to calculate the measured OA of the sheath at, e.g., a number of intervals along a rotation by comparing the reflection from the outer surface of the sheath with that from the inner surface, and apply the necessary rotation along every pixel of the A-line in a given interval in order to rotate the measured OA of the sheath to the actual OA as shown in FIGS. 16(a)-16(d), according to the exemplary equations:

$$A_n = <1,0,0> \times OA_n \quad (3)$$

$$\theta_n = \arctan \frac{|A_n|}{<1,0,0> \cdot OA_n} \quad (4)$$

$$OA_{ij,corr} = OA_{ij}\cos(\theta_i) + (A_i \times OA_{ij})\sin(\theta_i) + A_i(A_i \cdot OA_{ij})(1-\cos(\theta_i)) \quad (5)$$

where $A_n$ and $OA_n$ are the axis and the angle of rotation, respectively, for A-line n, and the correction is applied to every pixel at location i,j to obtain the corrected axis values $PA_{ij,corr}$. This approach allows us to accurately resolve the components of birefringence that lie along the same axis as the OA of the sheath, in Stokes space (and those only). In the physical cylindrical space of the sheath and surrounding tissue, this corresponds to both the longitudinal and circumferential components of the OA, as shown in FIGS. 16(a)-16(d). The variation of the components with imaging angle shown in these figures demonstrates a possible unreliability of uncalibrated OA measurements in endoscopic imaging. Scale bars, 1 mm. The exemplary procedure can be summarized in the following exemplary steps:

Input: Uncorrected OA; sheath position along frame (obtained from curve fitting algorithm)
 a. Divide frame into 128 vertical segments (8 unique A-lines per segment). Compute average OA per segment.
 b. (Per segment) Calculate OA of sheath using eq.1 with z the position of the inner sheath edge and dz the position of the outer sheath edge.
 c. (Per segment) Calculate the rotation axis/angle between measured sheath OA and <1,0,0> according to eqs. 3 and 4.
 d. (Per segment) Apply the rotation to every pixel along depth according to eq. 5.
 e. Enforce consistency by calculating the rotation angle differential across segments. This step is necessary because $\pi$ shifts can occur when the measured OA crosses an axis in the U-V plane.
 f. Perform a second consistency check. If there exists a region in which the sheath signals are not well defined, polarimetry noise can cause the correction to fail. In this case we interpolate across any additional discontinuities using adjacent signal-strong segments.

Output: Corrected +/−Q axis components of the OA; unresolved U-V components of the OA.

Exemplary steps (e) and (f) above can rely on the polarization distortion along the frame being well-behaved; i.e., the transmitted polarization state is smoothly varying. This exemplary assumption to hold even in the clinical setting, where the handling of the endoscopic probe is at its most fluid. This exemplary procedure was validated using orthogonally oriented stretched rubber phantoms (see FIGS. 17(a)-17(c))—with the exemplary endoscopic probe being inserted between the two phantoms along the axis of the bottom one (scale bars, 1 mm), as well as in the airway where self-consistency and correlation with bench-top data suggest accurate and robust performance (see FIGS. 18(a)-18(d)). The exemplary correction procedure employed in the exemplary embodiment that generated FIGS. 18(a)-18(d) does not resolve the U and V axes. Again, scale bars in these figures are at 1 mm.

Tissue Contour Adaptive Filtering

An exemplary averaging filter can be applied to the Stokes vectors before such vectors are used to calculate the birefringence of the sample in order to reduce the granulated appearance that results from speckle in the intensity data and make the data easier to interpret. The averaging procedure used to the spectral binning procedure can render further axial averaging unnecessary, but lateral filtering still has a drastic effect on the final image. Previously, a similar filtering technique was applied regardless of imaging conditions, viz. a fixed-orientation kernel was employed to filter the matrices corresponding to each of the components of the Stokes vector individually and column-wise only (see FIGS. 19(a)-19(f) —with scale bars at 1 mm.). This exemplary approach can be effective in situations where (e.g., in bench-top imaging) the tissue is approximately flat, or, in endoscopic imaging, the tissue is approximately circular and the probe well-centered. As the angle of the tissue with respect to the k-vector of the probing light increases, however, the filtering can become less beneficial in situations where the features of interest follow the contour of the tissue lumen. This can be the case in the case of ASM.

As a more suitable solution to this problem, it is possible to utilize an exemplary procedure that considers the slope of the tissue when performing Stokes averaging. The general approach of such exemplary procedure can be outlined as follows:
 a. Find the axial position of the tissue lumen per A-line using automatic segmentation.
 b. Fit a curve from the array of axial positions.
 c. Take the derivative to find the slope of the curve at a given A-line.
 d. Take a linear Gaussian averaging kernel and rotate it so that it is oriented along the slope at that A-line.
 e. Repeat steps 3 and 4 for every A-line in the frame.

A 12-pixel Stokes averaging kernel was employed for all of the PS data presented in this work. Using this exemplary approach, it is possible to obtain exemplary results that were more consistent with histology, particularly where the angle of the tissue was steep (see FIGS. 19(a)-19(f)).

Exemplary Circularization and Refractive Index Compensation

Using an exemplary fixed pixel resolution can result in obtaining data that is somewhat skewed in proportions due to the differing refractive indices (and therefore light propagation delays) between air and tissue. To compensate for this, it is possible to take the air pixels between the sheath and the tissue lumen and re-interpolate them so that the pixel resolution in air matches the pixel resolution in tissue. This exemplary approach can provide a more accurate geometrical representation of the tissue (see FIGS. 20(a)-20(g)). It can also have the added benefit of correcting for apparent tissue discontinuities that arise at air/mucus interfaces. The rectangular data can then be converted into a polar representation, and the scale can be set according to the pixel metric in tissue (e.g., 7 µm for a 2048×2048 pixel polar frame). The radial offset can be adjusted so that the measured diameter of the sheath matches the actual diameter.

Exemplary Determination of ASM Areas in PS-OCT and Histology

Imaged airway segments were fixed in formalin for 48 hours and submitted for histology. Section intervals were selected on a per-segment basis, determined such that approximately 10 sections were obtained per segment. Of these 10 sections, 5 were selected for matching. They were chosen based on the following criteria: whether the airway was closed; whether the epithelium was intact; and whether there were any other significant blemishes or tissue damage. Each slide selected was then matched to an OCT frame. Both H&E (for matching) and □SM-actin (for assessing ASM) stains were digitized using a Nanozoomer 2.0RS (Hamamatsu Corp.) at magnifications ranging from 1.25-40×, with the appropriate scales integrated into the outputted images. Manual segmentation of the ASM and computation of the ASM areas in the images were done in imageJ, with a separate individual being responsible for the matching of slides, histology segmentation, and PS-OCT segmentation. Segmentation of the ASM in histology was performed using images digitized at 5× magnification. For the PS-OCT segmentation, both the OA image and the structural image were used. It was necessary to refer to the structural image in cases where circumferentially oriented perichondrium closely abutted the ASM layer.

Exemplary Force of Contraction and Change in Birefringence

An exemplary setup for recording the force of contraction while imaging a tracheal segment included an exemplary microscope design in which galvanometric mirrors raster scanned the beam, and a force transducer connected to one side of a tracheal segment via string and tissue clip. The other side of the tracheal segment was fixed to a post with a pin (See FIGS. 21($a$) and 21($b$)). As shown in FIG. 21($b$), light (or other electro-magnetic radiation) from the PS-OCT fiber was coupled into the bench-top microscope using a fiber collimator (FC). Galvanometric mirrors (GM) controlled the position of the beam, which was focused onto the tissue sample with a telecentric objective lens (effective focal length 36 mm) (Thorlabs, Inc.). The force was recorded with a force transducer (FT) which was attached to one end of the tissue sample via a taut thread The tension on the string was adjusted so that the tracheal segment was slightly taut (~10% above resting tension), and the transducer was zeroed. Approximately 1 mL of methacholine was then applied to the segment using a pipette, and simultaneously the transducer output and PS-OCT images were recorded. Data was collected until the force of contraction had leveled off. For the isolated trachealis muscle experiment the muscle was dissected using a dissecting microscope and the same procedure was followed.

Exemplary ASM Thickness Comparison in Asthmatic and Non-Asthmatic Subjects

Clinical Imaging Procedure. Volunteers were enrolled in a clinical study and subject to a bronchoscopy while under sedation. The pulmonologist performing the procedure guided the bronchoscope to the appropriate bronchus in the right upper lobe of the subject and the PS-OCT endoscopic probe was then threaded through the bronchoscope channel and out 3 cm into the bronchus. The pullback rate was 1 mm/s, resulting in a total imaging time of 30 seconds.

Exemplary ASM Thickness Processing. The ASM layer was manually segmented for all the frames in the volumetric dataset. Thickness was computed by the non-zero circumferential OA pixels and converting to a physical length according to the pixel metric in tissue (3.53 μm). To render the volumetric images as accurate as possible, the curvature of the airway with respect to the imaging probe was considered by counting the thickness along the normal to the tissue lumen, rather than simply along each A-line individually. Longitudinal cross-section locations were selected in part for their degree of flatness in order to avoid any loss of birefringence due to fiber orientation.

Exemplary Cross-Sectional Calculations. Peaks were identified by calculating local maxima and thresholded at a value of 0.001 mm ASM thickness/mm airway perimeter. Amplitude was calculated by taking the larger of the two peak heights as calculated from local minima on either side of the peak. Periodicity and width were determined by counting the distance between peaks and peak width (as measured from adjacent minima) and converting to longitudinal distance according to the probe pullback pitch (30 μm).

Exemplary Testing

For the in vivo human data, the imaging probe was threaded through the working channel of a bronchoscope and extended a length of 3 cm beyond into the airway. The pullback of the probe was synchronized with the start of data recording, and translated at a rate of 1 mm/s until the probe returned to the bronchoscope channel aperture. We derived cross-sectional images of ASM distributions in the airway by overlaying the circumferential OA component map on the intensity map obtained by conventional means (FIG. 22($a$)). To obtain the retardance associated with the ASM band, we have weighted the OA map with the local retardance map (FIG. 22($b$)). Colormaps were deliberately chosen to distinguish the binary nature of the OA (red, indicating presence of ASM) from the nuanced retardance (jet, degree of ASM birefringence). The significance of the retardance is explored in a proceeding section. In addition to cross-sections, we have constructed three-dimensional images from the fully continuous data stacks (FIGS. 22($c$) and 22($d$)), facilitating a more comprehensive qualitative analysis of the ASM banding. In addition to OA isolation, several exemplary processing techniques were employed to more accurately represent the data depicted here. These include spectral binning of the polarization data to reduce the impact of polarization mode dispersion, as well as novel techniques for filtering and circularizing the data, as shown in FIGS. 19 and 20, respectively. The exemplary structural images are presented in FIGS. 22($a$)-22($d$) in grayscale and the circumferential component of the OA, corresponding to the orientation of ASM, is overlaid. The quasi-monochromaticity of the OA colormap is representative of the fact that, in contrast with the sample retardance, OA is treated as a binary quantity indicating the presence or absence of ASM.

Validation with Exemplary Histology

An exemplary goal of imaging ASM can be to be able to assess ASM densities in the airway in vivo, and with an accuracy comparable to that of histology. In order to perform validation of the exemplary results, airway segments from both swine and canine lungs were imaged ex vivo, and histological sections were afterwards obtained from the same segments and matched with OCT images for correlation assessment. Swine lungs were obtained within 1-2 hours of the subject's sacrifice. Lungs were obtained from three different pigs, with a total of 17 airway segments imaged, ranging in diameter from 3-7 mm and length of 1-2 cm. One set of canine lungs were obtained. These were excised from the canine sacrifice at an off-site facility, where they were immersed in a Krebs-Henseleit buffer and shipped to our laboratory overnight. Similar to the swine lungs, 19 canine airway segments were imaged, ranging in diameter from 2-5 mm and a length of 1-2 cm. Immediately prior to imaging a given segment, a saline flush was performed. The probe pullback rate for excised airway segments was 0.5 mm/s.

For histology correlation, sections were cut every 1 mm and stained with H&E, for structural matching, as well as alpha smooth muscle actin, in order to highlight the ASM. The matching of intensity-based (non-PS) OCT frames to histology slides was performed without referencing either the birefringence maps of the associated OCT data or the alpha smooth muscle stains of the histology. Manual segmentation of the ASM areas in the PS-OCT images was performed by a PS-OCT expert and those of the histology was performed by a pathologist. The ASM areas in both data sets were calculated. Further details on this process, as well as a description of how the PS-OCT processing parameters, including intensity-weighting and thresholding, were determined and implemented are described herein above.

Figure 23E:
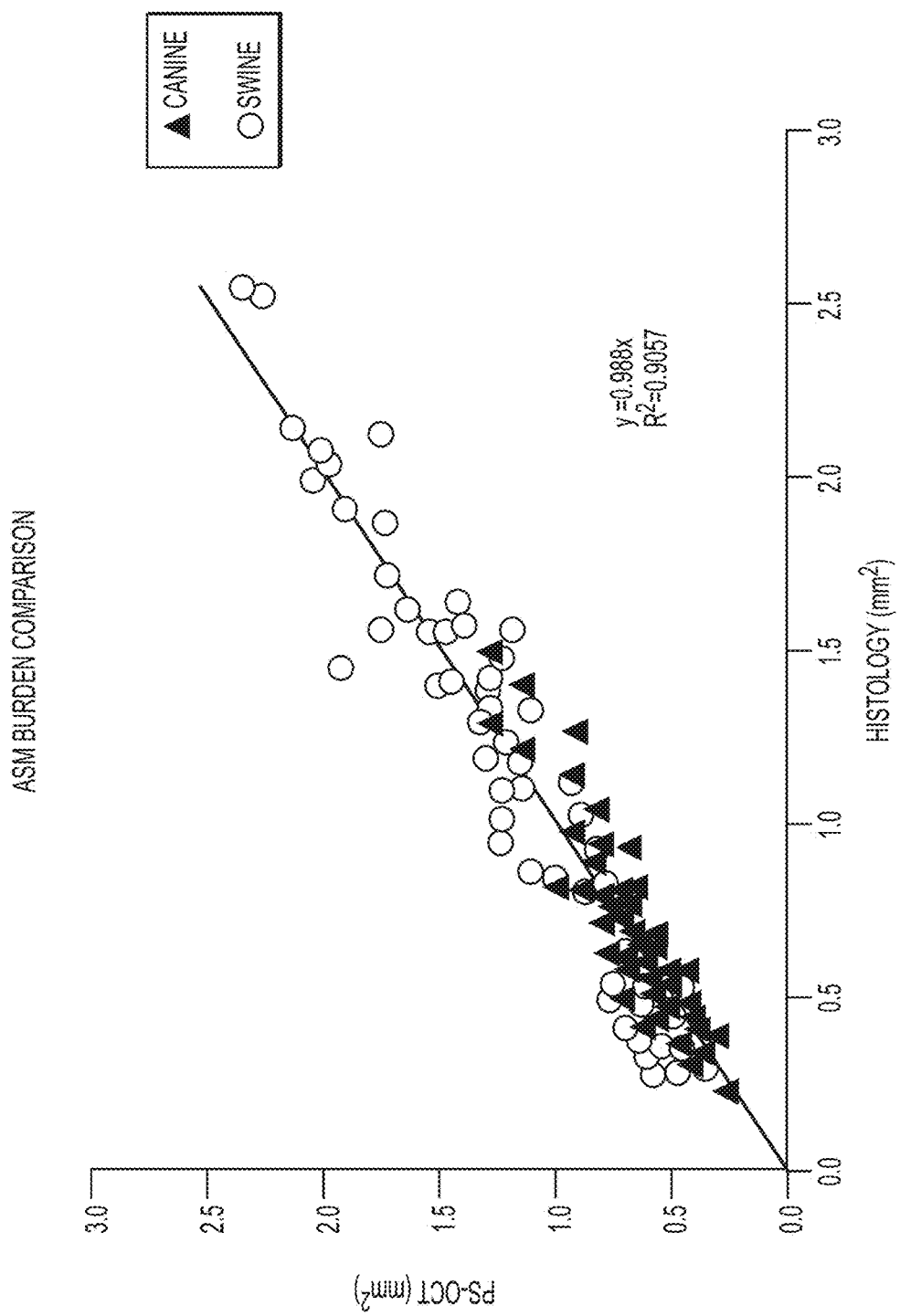
FIG. 23(e) is a graph providing an exemplary assessments obtained with the exemplary PS-OCT system and method, compared with those from the histology.
Figure 24A:
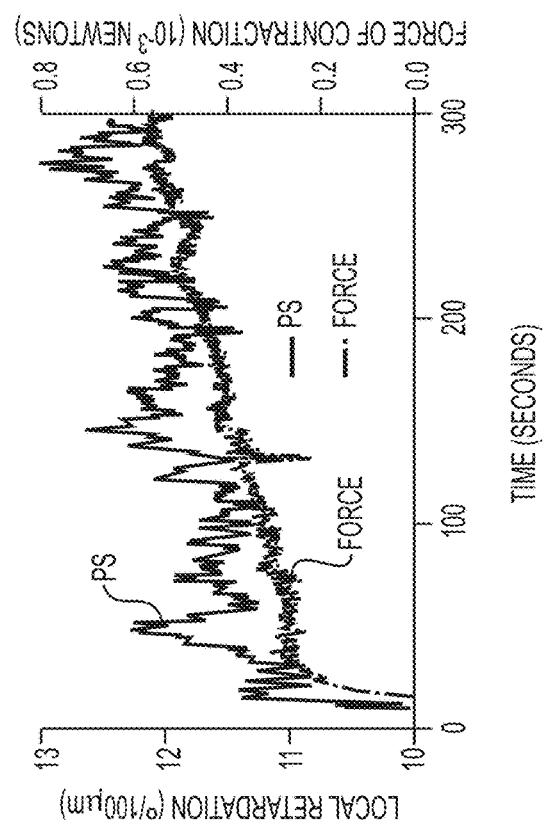
FIG. 24(a) is a PS-OCT image depicting a cross section of a canine bronchiole.
Figure 24B:
FIG. 24(b) is an illustration of a corresponding histology match, stained with alpha smooth muscle actin and the slide being digitized at 5× magnification.
Figure 24C:
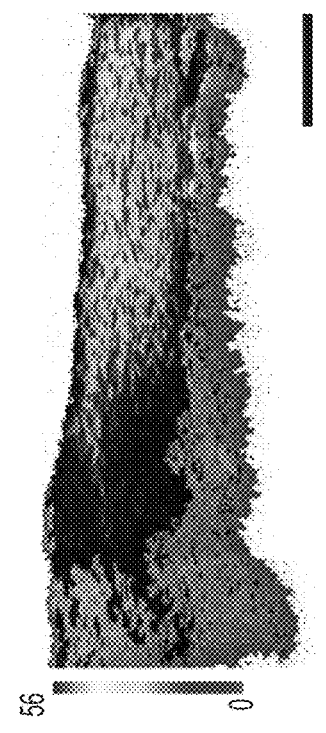
FIGS. 24(c) and (f) are graphs providing an exemplary assessments obtained with the exemplary PS-OCT system and method, compared with those from the histology.
Figures 24D, 24E, 24F:
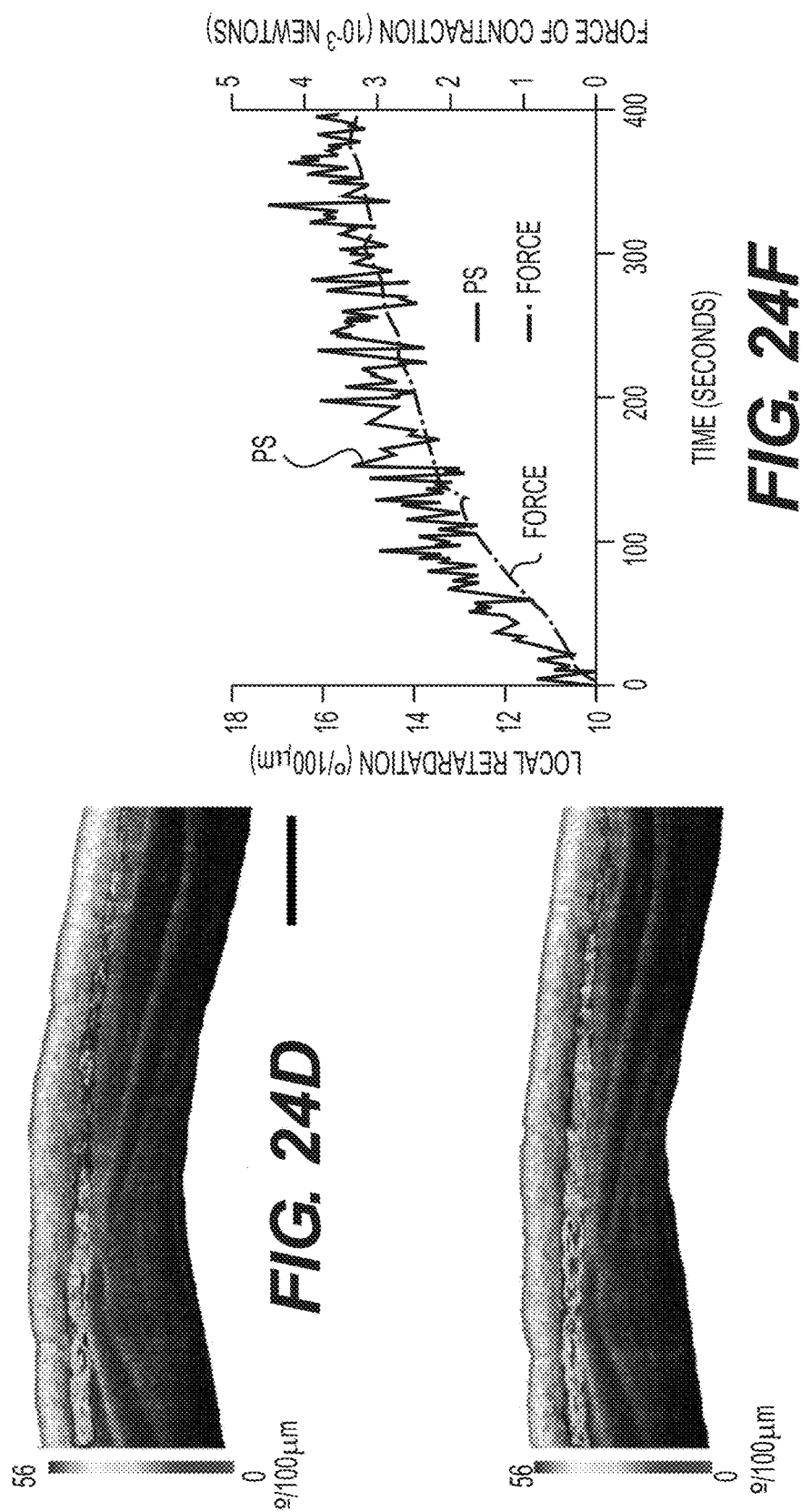
FIGS. 24(e) and (d) are PS-OCT image frame and matching histology, respectively, from a swine bronchiole, obtained in substantially the same manner as described for the canine match.

As a result of the assessments, PS-OCT area estimates were determined to be highly correlated with those of histology (see FIG. 23(c)). Considered separately, the 80 matches for the canine assessments had an $R^2$ of 0.81, whereas the 82 swine matches had an $R^2$ of 0.92. We attribute this discrepancy to the increased tissue degradation of the canine lungs, which is known to have a deleterious effect on image fidelity. Compared to swine bronchi, which possess clean, ordered tissue layers with minimal perichondria, canine bronchi are also much more irregular, with an increased abundance of both ASM and perichondrial tissue, particularly in the more distal airways. Though the perichondrium does not have a fixed orientation like ASM does, we believe it may also contribute to false-positive ASM signal in cases where the two layers are closely adjoined. The data obtained, as shown in FIGS. 23(a)-23(e) comprises, e.g., 162 matches, including 82 matches obtained from 17 segments of swine bronchi ranging in diameter from 3-7 mm, and 80 matches obtained from 17 segments of canine bronchi ranging in diameter from 2-5 mm. Scale bars provided in these figures are at 1 mm.

Exemplary Volumetric Morphology Comparison

While cross-sectional analysis is useful for investigating localized details, volumetric reconstructions offer the advantage of bringing into relief gross airway characteristics such as ASM band density and distribution. Though extensive literature exists detailing the thickening of ASM in asthmatic lungs, little attention has been given to the broad morphological alterations engendered by the disease—due, naturally, to the difficulty associated with observing such changes. To provide some insight into these changes as well as demonstrating the potential role of our platform in monitoring the morphological effects of the disease, in vivo imaging has been performed using the exemplary embodiments of the systems and methods according to an exemplary embodiment of the present disclosure of both non-asthmatic and asthmatic subjects in bronchi of comparable location and diameter and analyzed the observable differences between the two (see, e.g., FIGS. 24(a)-24(f)). To bring the an exemplary usable radial ASM parameter, the thickness, into relief, it is possible to parameterize the volumetric reconstructions in terms of ASM thickness by performing pixel counting with the OA data, as described herein above.

Indeed, FIGS. 24(a)-24(f) illustrate an exemplary stimulated contraction of tracheal smooth muscle strips. The strips were fixed to a force transducer and contraction was induced by the application acetyl methacholine. PS-OCT images are represented by structural (grayscale) overlaid with local retardance. Scale bars provided in these figures are at 1 mm.

For example, using the thickness-encoded volumetric data, several morphological comparisons can be made. The mean ASM thickness (thickness/lumen perimeter) was 34 μm (0.0025) for the non-asthmatic airway and 59 um (0.0039) for the asthmatic airway. Taking a longitudinal cross-section for both data sets extending 13 mm in length and located away from branch points, we observe the following characteristics: for the non-asthmatic airway; a mean band periodicity of 512 μm, a mean band amplitude of 28 μm (0.0021), and a mean band width (base to peak) of 410 μm. For the asthmatic airway; a mean band periodicity of 466 μm, a mean band amplitude of 26 μm (0.0017), and a mean band width of 410 μm. We note that the values that for mean ASM thickness have been obtained as consistent with previously published results, while further illuminating finer points of similarity (band amplitude, band width) and distinction (band periodicity, band baseline thickness) between the two airways.

Exemplary ASM Contraction and PS-OCT Retardance

In contrast with OA, which is indicative of the presence and orientation of birefringent tissue, retardance can be associated with the density and degree of order of the birefringent elements. Previous work using polarized light microscopy determined that the bulk birefringence of excised ASM muscle strips increased during muscle contraction. Though interesting and of clear academic value, this exemplary approach offers no viable pathway for studying muscle contraction in vivo. In order to determine whether PS-OCT can be used to observe a similar effect, our PS-OCT system was set up in a bench-top microscope configuration for imaging both isolated trachealis muscle strips and intact trachealis sections. The tissue was mounted onto a force transducer and contraction of the strip was stimulated using methacholine. During contraction the exerted force was measured concurrently with PS-OCT image acquisition (see, e.g., FIG. 21). Comparison between the force and the local retardance of the muscle tissue (taken as an average per frame) yielded similar time curves in both cases. Time elapse movies of the contractions as recorded with PS-OCT offer additional qualitative insight into the structural and birefringence changes as they occur locally.

To further establish the groundwork for applying these results in an in vivo setting, we have also investigated changes in birefringence during contraction for the case of a length of bronchus imaged with our endoscopic probe. Exemplary volumetric imaging of a length of swine bronchus segment was performed at two separate time points corresponding to the at rest and contracted states by performing an initial catheter pullback scan and then performing the same scan five minutes after the application of methacholine (see FIGS. 25(a)-25(j)). It is possible to plot the change in airway area, along with the change in OA and the change in retardation. The results are elucidating. The mean airway area decreased by 21.3%, and while the mean OA also decreased, by 1%, the mean retardation increased by 23.3%. This minuscule decrease in ASM presence can be attributable to the compression of the ASM layer under contraction. These results then reinforce the distinction between OA as the primary indicator of ASM and local retardation as the indicator of contractility. Indeed, FIGS. 25(a)-25(f) illustrate data for a stimulated contraction of tracheal smooth muscle strips. The strips were fixed to a force transducer and contraction was induced by the application acetyl methacholine. Exemplary PS-OCT images are represented in these figures by structural (grayscale) overlaid with a local retardation. For FIG. 25(c), the local retardation data points were obtained by taking the mean local retardation in a given frame of all pixels identified by the OA and structural maps as being smooth muscle.

Figure 25C:
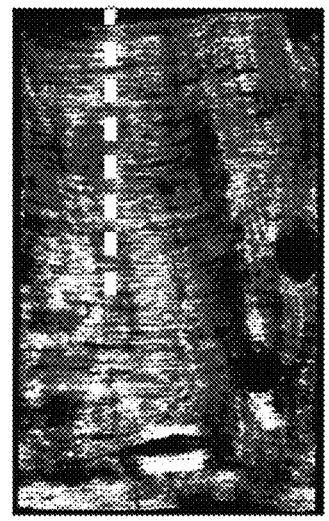
FIG. 25(c) is an illustration of an exemplary circularized image of an asthmatic subject.
Figure 25D:
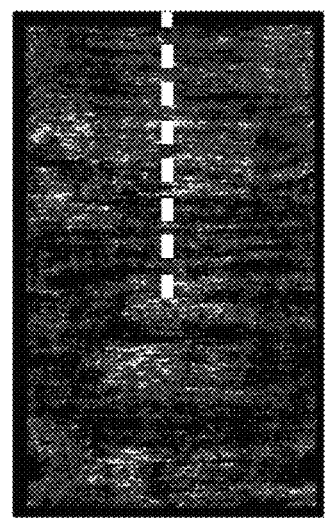
FIG. 25(d) is an exemplary flattened image for such asthmatic subject.
Figure 25A:
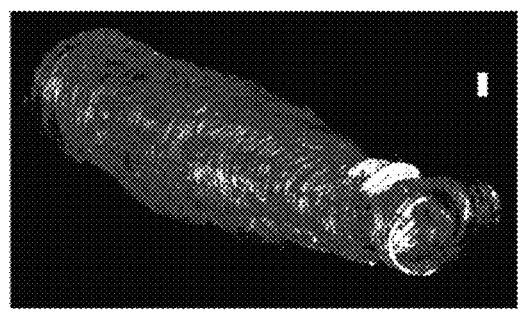
FIG. 25(a) is an illustration of an exemplary circularized volumetric image from a 2.4 cm endoscopic probe pullback of the non-asthmatic subject.
Figure 25B:
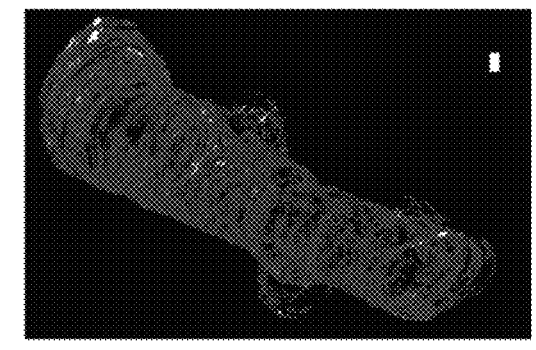
FIG. 25(b) is an image of an exemplary flattened representation of the same data

FIGS. 25(a)-25(i) are illustrations and graphs of Morphological comparison between asthmatic and non-asthmatic human subjects, in vivo. FIG. 25(a) shows an illustration of an exemplary circularized volumetric image from a 2.4 cm endoscopic probe pullback of the non-asthmatic subject. The plotted quantity is the ratio of ASM thickness to airway perimeter, as calculated from the ASM OA data and fitted lumen curves. FIG. 25(b) shows an image of an exemplary flattened representation of the same data. FIG. 25(c) shows an illustration of an exemplary circularized image of an asthmatic subject, also from a 2.4 cm pullback, plotted with the same metric and scale as for the non-asthmatic subject. FIG. 25(d) illustrates an exemplary flattened image for such asthmatic subject. Both images of FIGS. 25(c) and 25(d) were acquired from similar regions of the lung in the right upper lobe. FIG. 25(e) shows a graph of an exemplary absolute thickness profile from a 1.3 cm longitudinal cross section of the non-asthmatic bronchus (region indicated with dashed line in FIG. 25(b). FIG. 25(f) illustrates a graph of an exemplary thickness profile of the image shown in FIG. 25(e), divided by lumen perimeter measured at the corresponding longitudinal position, with peak positions indicated with arrows. FIGS. 25(g) and 25(h) illustrate graphs of the same profiles for the asthmatic bronchus. FIG. 25(i) shows a graph of an exemplary airway perimeter as a function of pullback location for non-asthmatic, and FIG. 25(j) illustrates a similar graph of the asthmatic airway. Scale bars shown in these figures are at 1 mm.

Figures 26A, 26C:
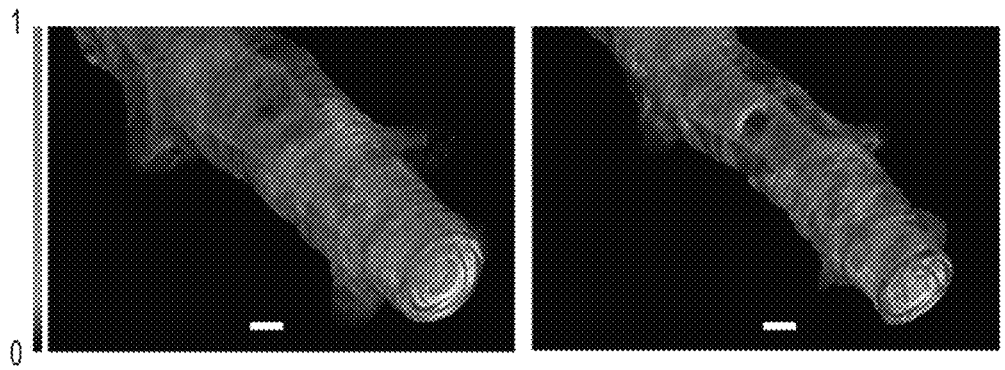
FIGS. 26(a) and 26(b) are illustrations of an 1.58 cm ex vivo segment imaged before the application of acetyl methacholine.
FIGS. 26(c) and 26(d) are illustration of the segment imaged five minutes after the application of acetyl methacholine.
Figures 26B, 26D:
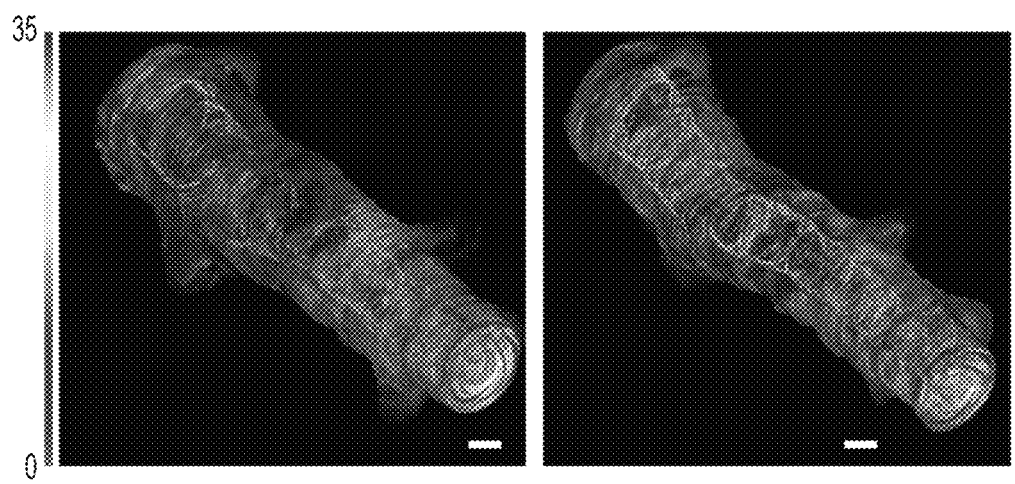
Figures 26E, 26F, 26G:
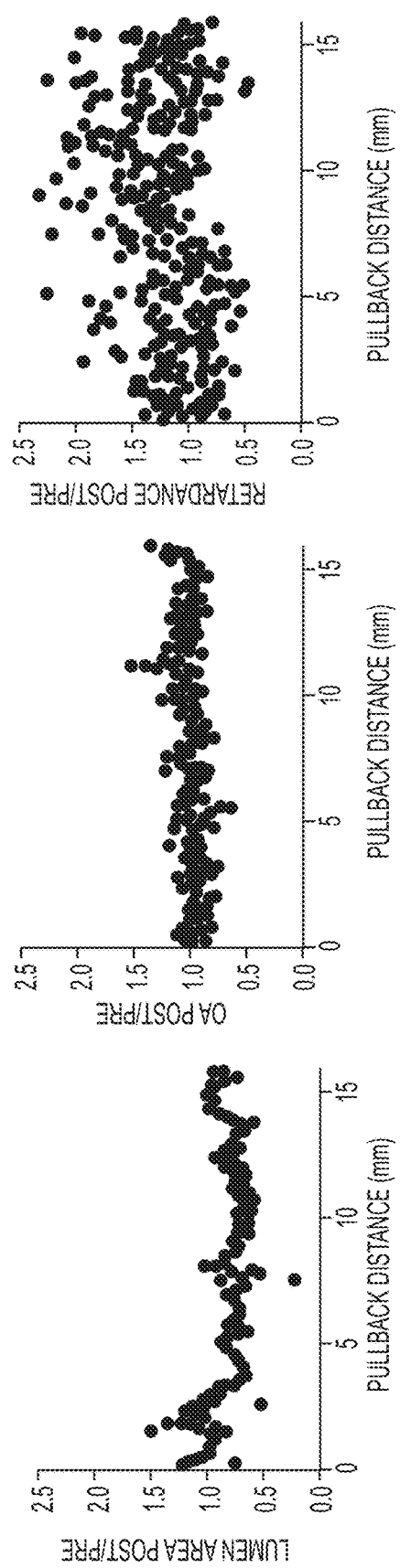
FIGS. 26(e)-26(g) are exemplary graphs of a number of parameter ratios (post-methacholine to pre-methacholine) per matched frame along the entire segment.

As shown in FIGS. 26(a)-26(g), illustrations and graphs for contracted and reference states for a length of swine bronchiole are provided. For example, as illustrated in FIGS. 26(a) and 26(b), a 1.58 cm ex vivo segment was imaged before, and as shown in FIGS. 26(c) and 26(d)—five minutes after the application of acetyl methacholine. Volumetric renderings are depicted with OA (as shown in FIGS. 26(a) and 26(c)) and local retardation (as shown in FIGS. 26(b) and 26(d)) overlaid. FIGS. 26(e)-26(g) illustrate graphs of a number of parameter ratios (post-methacholine to pre-methacholine) per matched frame along the entire segment. The rations of area (as provided in graph of FIG. 26(e)), OA (as provided in graph of FIG. 26(f)), and retardation (as provided in graph of FIG. 26(g)) were plotted. Exemplary mean percent changes (averaged over entire segment) are as follows: area −21.3%; OA −1.0%; retardation +23.3%. The drop in OA (the amount of ASM detected) is likely due to compression of ASM bundles in the contracted state. Scale bars shown in these figures are at 1 mm.

Exemplary Discussion

By utilizing the intrinsic capabilities of PS-OCT, as well as introducing several novel data extraction and processing techniques, a comprehensive platform for investigating ASM distributions in the airways. Compatibility with standard fiber-based imaging probes facilitates such exemplary technology to be employed in vivo during bronchoscopy procedure, with minimal additional demands placed on the clinician or patient. For the prioritization of efficient image acquisition during clinical procedures, a pullback rate of about 1 mm/s, corresponding to a longitudinal pitch of 30 µm, offers ample resolution for performing morphological analysis. Using this approach, it is possible to evaluate volumetrically ASM morphology, including banding and thickness, as well as contractile parameters through the association of muscle birefringence with force of contraction.

Operating within the limits of standard PS-OCT technology, it is possible to identify ASM densities commensurate with assessments performed by a pathologist viewing histological stains digitized at 5× magnification. These exemplary results can be complimented by the demonstration of a close relationship between force of contraction and local retardance of ASM bundles, illustrating the potential for further investigation into muscle and airway dynamics. In addition to establishing these capabilities, exemplary imaging has been performed and compared ASM distributions in living asthmatic and non-asthmatic subjects. Going beyond broad ASM thickness comparison, it is possible to utilize volumetric datasets to perform an exemplary analysis of the overall structure and composition of ASM in the bronchi and showed contrasting results of a more subtle nature such as ASM band periodicity. The robustness of this exemplary platform facilitates immediate clinical implementation and the ability to observe structure and effect to a degree not previously available.

The foregoing merely illustrates the principles of the disclosure. Various modifications and alterations to the described embodiments will be apparent to those skilled in the art in view of the teachings herein. Indeed, the arrangements, systems and methods according to the exemplary embodiments of the present disclosure can be used with and/or implement any OCT system, OFDI system, SD-OCT system or other imaging systems, and for example with those described in International Patent Application PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, and U.S. Patent Publication No. 2002/0122246, published on May 9, 2002, the disclosures of which are incorporated by reference herein in their entireties. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly being incorporated herein in its entirety. All publications referenced above can be incorporated herein by reference in their entireties.

Exemplary references, the entire disclosure of which is incorporated herein by reference:

1. Wang H, Al-Qaisi M K, Akkin T: Polarization . . . maintaining fiber based polarization-sensitive optical coherence tomography in spectral domain. *Opt Lett* 2010, 35(2):154-156.
2. Lu Z, Matcher S J: Absolute fast axis determination using non-polarization maintaining fiber-based polarizationsensitive optical coherence tomography. *Opt Lett* 2012, 37(11)1931-1933.
3. Villiger M, Zhang E Z, Nadkarni S, Oh W-Y, Vakoc B, Bouma B E: Spectral binning for mitigation of polarization mode dispersion artifacts in catheter-based optical frequency domain imaging. *Opt Exp* 2013, 21(14)16353-16369.
4. Saxer C E, de Boer J F, Park B H, Zhao Y H, Chen Z P, and Nelson J S: High-speed fiber based polarization-sensitive optical coherence tomography of in vivo human skin. *Opt Lett* 2000, 25(18):1355-1357.
5. Park B, Pierce M, Cense B, de Boer J F: Realtime multi-functional optical coherence tomography. *Opt Exp* 2003, 11(7):782-793.
6. Yun S H, Tearney G J, Vakoc B J, Shishkov M, Oh W Y, Desjardins A E, Suter M J, Chan R C, Evans J A, Jang I K et al: Comprehensive volumetric optical microscopy in vivo. *Nat Med* 2006, 12(12):1429-1433.
7. Nadkarni S K, Pierce M C, Park B H, de Boer J F, Whittaker P, Bouma B E, Bressner J E, Halpern E, Houser S L, Tearney G J: Measurement of collagen and smooth muscle cell content in atherosclerotic plaques using polarization-sensitive optical coherence tomography. *Journal of the American College of Cardiology* 2007, 49(13): 1474-1481.
8. Woodruff, P. G., et al. Hyperplasia of smooth muscle in mild to moderate asthma without changes in cell size or gene expression. American journal of respiratory and critical care medicine 169, 1001-1006 (2004).
9. Castro, M., et al. Effectiveness and safety of bronchial thermoplasty in the treatment of severe asthma: a multi-center, randomized, double-blind, sham-controlled clinical trial. American journal of respiratory and critical care medicine 181, 116-124 (2010).
10. Bosse, Y. Asthmatic airway hyperresponsiveness: the ants in the tree. Trends in molecular medicine 18, 627-633 (2012).
11. Wenzel, S. E. Asthma phenotypes: the evolution from clinical to molecular approaches. Nature medicine 18, 716-725 (2012).
12. Sittka, A., Vera, J., Lai, X. & Schmeck, B. T. Asthma phenotyping, therapy, and prevention: what can we learn from systems biology? Pediatric research 73, 543-552 (2013).
13. Huang, D., et al. Optical coherence tomography. Science 254, 1178-1181 (1991).
14. de Boer, J. F., Milner, T. E., van Gemert, M. J. & Nelson, J. S. Two-dimensional birefringence imaging in biological tissue by polarization-sensitive optical coherence tomography. Optics letters 22, 934-936 (1997).
15. Saxer, C. E., et al. High-speed fiber based polarization-sensitive optical coherence tomography of in vivo human skin. Optics letters 25, 1355-1357 (2000).
16. Hitzenberger, C., Goetzinger, E., Sticker, M., Pircher, M. & Fercher, A. Measurement and imaging of birefringence and optic axis orientation by phase resolved polarization sensitive optical coherence tomography. Optics express 9, 780-790 (2001).
17. Oh, W. Y., et al. High-speed polarization sensitive optical frequency domain imaging with frequency multiplexing. Optics express 16, 1096-1103 (2008).
18. Nadkarni, S. K., et al. Measurement of collagen and smooth muscle cell content in atherosclerotic plaques using polarization-sensitive optical coherence tomography. Journal of the American College of Cardiology 49, 1474-1481 (2007).
19. Yun, S., Tearney, G., de Boer, J., Iftimia, N. & Bouma, B. High-speed optical frequency-domain imaging. Optics express 11, 2953-2963 (2003).
20. Villiger, M., et al. Spectral binning for mitigation of polarization mode dispersion artifacts in catheter-based optical frequency domain imaging. Optics express 21, 16353-16369 (2013).
21. Zhang, E. Z. & Vakoc, B. J. Polarimetry noise in fiber-based optical coherence tomography instrumentation. Optics express 19, 16830-16842 (2011).
22. Hsiung, P. L., Nambiar, P. R. & Fujimoto, J. G. Effect of tissue preservation on imaging using ultrahigh resolution optical coherence tomography. Journal of biomedical optics 10, 064033 (2005).
23. Carroll, N., Elliot, J., Morton, A. & James, A. The structure of large and small airways in nonfatal and fatal asthma. The American review of respiratory disease 147, 405-410 (1993).
24. Bara, I., Ozier, A., Tunon de Lara, J. M., Marthan, R. & Berger, P. Pathophysiology of bronchial smooth muscle remodelling in asthma. The European respiratory journal 36, 1174-1184 (2010).
25. James, A. & Carroll, N. Airway smooth muscle in health and disease; methods of measurement and relation to function. The European respiratory journal 15, 782-789 (2000).
26. Gillis, J. M., Cao, M. L. & Godfraind-De Becker, A. Density of myosin filaments in the rat anococcygeus muscle, at rest and in contraction. II. Journal of muscle research and cell motility 9, 18-29 (1988).
27. Godfraind-De Becker, A. & Gillis, J. M. Analysis of the birefringence of the smooth muscle anococcygeus of the rat, at rest and in contraction. I. Journal of muscle research and cell motility 9, 9-17 (1988).
28. Smolensky, A. V. & Ford, L. E. Filament lattice changes in smooth muscle assessed using birefringence. Canadian journal of physiology and pharmacology 83, 933-940 (2005).
29. Smolensky, A. V., Ragozzino, J., Gilbert, S. H., Seow, C. Y. & Ford, L. E. Length-dependent filament formation assessed from birefringence increases during activation of porcine tracheal muscle. The Journal of physiology 563, 517-527 (2005).
30. Yun, S., Tearney, G., de Boer, J. & Bouma, B. Removing the depth-degeneracy in optical frequency domain imaging with frequency shifting. Optics express 12, 4822-4828 (2004).
31. Park, B., Pierce, M., Cense, B. & de Boer, J. Real-time multi-functional optical coherence tomography. Optics express 11, 782-793 (2003).
32. Gordon, J. P. & Kogelnik, H. PMD fundamentals: polarization mode dispersion in optical fibers. Proceedings of the National Academy of Sciences of the United States of America 97, 4541-4550 (2000).

What is claimed is:
1. An apparatus, comprising:
at least one source which is configured to provide at least one first radiation;

at least one optical configuration which includes at least one catheter portion which is provided in an optical path between the at least one source and at least one sample, wherein the at least one catheter portion has at least one birefringent property;

at least one detector which is configured to receive at least one second radiation from at least one first section of the at least one catheter portion and at least one third radiation from at least one second section of the at least one catheter portion, wherein the second and third radiations are associated with the at least one first radiation; and at least one computer which is configured to determine information regarding at least one of the at least one sample or the at least one catheter portion based on the second and third radiations.

2. The apparatus according to claim 1, wherein the information includes an optical axis of the at least one catheter portion.

3. The apparatus according to claim 1, wherein the at least one computer further receives first data regarding at least one fourth radiation provided from the at least one sample, and generates second data regarding the at least one sample using the information and the first data.

4. The apparatus according to claim 3, wherein the at least one computer is further configured to generate at least one image of at least one portion of the at least one sample based on the second data.

5. The apparatus according to claim 4, wherein the at least one computer is further configured to correct at least one section of the at least one image based on at least one group of A-lines of at least one of (i) the second radiation, or (ii) the third radiation.

6. The apparatus according to claim 5, wherein the correction of the at least one section of the at least one image is performed for all of the A-lines.

7. The apparatus according to claim 6, wherein the first and second sections are provided on or in a handheld device, or a non-stationary device.

8. The apparatus according to claim 3, wherein the at least one computer determines at least two polarization states of the at least one fourth radiation, and wherein the at least one detector includes at least two separate structures.

9. The apparatus according to claim 8, wherein one of the structures has a material that is different from that of another one of the structures.

10. The apparatus according to claim 1, wherein the at least one optical configuration includes at least one third section that is non-stationary.

11. The apparatus according to claim 10, wherein the at least one third section of the at least one optical configuration includes an optical waveguide.

12. The apparatus according to claim 1, wherein the at least one first section of the at least one catheter portion is a first surface of the at least one catheter portion, and wherein the at least one second section of the at least one catheter portion is a second surface of the at least one catheter portion.

13. A method, comprising:
with at least one source, providing the at least one first radiation, which impacts at least one optical configuration including at least one catheter portion that is provided in an optical path between the at least one source and at least one sample, wherein the at least one catheter portion has at least one birefringent property;

with at least one detector, receiving at least one second radiation from at least one first section of the at least one catheter portion, and at least one third radiation from at least one second section of the at least one catheter portion, wherein the second and third radiations are associated with the at least one first radiation; and using at least one computer, determining information regarding at least one of the at least one sample or the at least one catheter portion based on the second and third radiations.

14. The method according to claim 13, wherein the information includes an optical axis of the at least one catheter portion.

15. The method according to claim 13, further comprising receiving at least one fourth radiation from the at least one sample, and generating data regarding the at least one sample using the information and the at least one fourth radiation.

16. The method according to claim 15, further comprising generating at least one image of at least one portion of the at least one sample based on the data.

17. The method according to claim 16, further comprising correcting at least one section of the at least one image based on at least one group of A-lines of at least one of (i) the second radiation, or (ii) the third radiation.

18. The method according to claim 17 wherein the correction of the at least one section of the at least one image is performed for all of the A-lines.

19. The method according to claim 18, wherein the first and second sections are provided on or in a handheld device, or a non-stationary device.

20. The method according to claim 16, further comprising determining at least two polarization states of the at least one fourth radiation.

21. The method according to claim 16, wherein the at least one optical configuration includes two separate structures.

22. The method according to claim 21, wherein one of the structures has a material that is different from that of another one of the structures.

23. The method according to claim 13, wherein the at least one catheter portion includes at least one third section that is non-stationary.

24. The method according to claim 23, wherein the at least one third section of the at least one catheter portion includes an optical waveguide.

25. The method according to claim 14, wherein the at least one first section of the at least one catheter portion is a first surface of the at least one catheter portion, and wherein the at least one second section of the at least one catheter portion is a second surface of the at least one catheter portion.

* * * * *